(12) United States Patent
Henley et al.

(10) Patent No.: US 9,927,340 B2
(45) Date of Patent: Mar. 27, 2018

(54) VIBRATION ANALYSIS FOR BLASTING

(71) Applicant: Orica International Pte Ltd, Singapore (SG)

(72) Inventors: Kim Nigel Henley, Tennyson (AU); Donald Scott Scovira, Highlands Ranch, CO (US); Alexander Theofile Spathis, Newcastle (AU); Ruilin Yang, Centennial, CO (US)

(73) Assignee: Orica International Pte Ltd, Singapore (SG)

( * ) Notice: Subject to any disclaimer, the term of this patent is extended or adjusted under 35 U.S.C. 154(b) by 759 days.

(21) Appl. No.: 14/356,858

(22) PCT Filed: Nov. 9, 2012

(86) PCT No.: PCT/AU2012/001378
§ 371 (c)(1),
(2) Date: May 7, 2014

(87) PCT Pub. No.: WO2013/067590
PCT Pub. Date: May 16, 2013

(65) Prior Publication Data
US 2014/0365143 A1 Dec. 11, 2014

Related U.S. Application Data

(60) Provisional application No. 61/558,978, filed on Nov. 11, 2011.

(51) Int. Cl.
*G01B 5/28* (2006.01)
*G01N 3/313* (2006.01)
(Continued)

(52) U.S. Cl.
CPC .............. *G01N 3/313* (2013.01); *G01H 17/00* (2013.01); *G01N 29/04* (2013.01); *G01N 29/44* (2013.01); *G01V 1/18* (2013.01); *G01N 2291/023* (2013.01); *G01N 2291/028* (2013.01); *G01N 2291/0423* (2013.01); *G01V 1/04* (2013.01)

(58) Field of Classification Search
CPC ........... G01N 29/04; G01N 2291/0423; G01N 29/44; G01N 2291/028; G01N 2291/023; G01N 3/313; G01V 1/18; G01V 1/04; G01H 17/00
See application file for complete search history.

(56) References Cited

U.S. PATENT DOCUMENTS 7,707,939 B2 * 5/2010 Brent ........................ F42D 1/00
102/312

OTHER PUBLICATIONS

International Search Report of PCT/AU2012/001378 dated Jan. 14, 2013, 7 pages.
(Continued)

*Primary Examiner* — Elias Desta
(74) *Attorney, Agent, or Firm* — Kilpatrick Townsend & Stockton LLP

(57) ABSTRACT

A process for vibration analysis, including the steps of: receiving synchronized motion measurements of particle motion in two or three orthogonal dimensions over a selected period of time at a plurality of different measurement locations; and determining one or more strain waveforms in the orthogonal dimensions in regions spanning the plurality of measurement locations using the motion measurements.

24 Claims, 8 Drawing Sheets

(51) Int. Cl.
    *G01H 17/00*     (2006.01)
    *G01N 29/04*     (2006.01)
    *G01N 29/44*     (2006.01)
    *G01V 1/18*     (2006.01)
    *G01V 1/04*     (2006.01)

(56) References Cited

OTHER PUBLICATIONS

Jayasuriyi, A.M.M., Finite element modeling of blast vibration and study of vibration control criteria, A Thesis Presented to the Faculty of the College of Engineering and Technology Ohio University, 1989, [retrieved on Jan. 8, 2013]. Ref to the whole document and in particular to abstract, chapter 2, p. 5-8, chapter 3.1 p. 33+, Table 3.1, chapter 4.2, p. 55-62, Table 2.5b, Figs. 4.4-4.7, p. 89-94 & 100, Figs. 5.10 and 5.11.

Allen, P, Seismic near field of an air gun measured by a wide band accelerometer system, M.S. Thesis, Massachusetts Institute of Technology, 1971, [retrieved on Jan. 8, 2013], Refer to whole document and in particular to p. 4-6.

Harvey, S et al., Tri-axial measurement of roadway vibration in multiple research buildings located throughout an urban college campus, The Journal of the Acoustical Society of America, 2010, vol. 127, Issue 3, pp. 1836-1836, [retrieved on Jan. 8, 2013].

Yang, R. et al., Using blast vibration measurements to estimate rock triaxial strains/stresses and dynamic rock strength for blast damage evaluation, Rock Mechanics: Meeting Society's Challenges and Demands—Eberhardt, Stead & Morrison (eds) © 2007 Taylor & Francis Group, London, ISBN 978-0-415-44401-9, pp. 1547-4552.

* cited by examiner

VIBRATION ANALYSIS FOR BLASTING

FIELD

The present invention relates to systems and processes for vibration analysis, e.g., for estimating two-dimensional (2D) or three-dimensional (3D) dynamic strain tensors in natural and/or man-made structures from vibrations produced by blasting, impacts or other man-made events.

BACKGROUND

Blasting events generally cause damage and stresses in the ground and/or in man-made structures, that extend beyond the immediate area or region of the event, e.g., outside the perimeter of a mining excavation. For example, blast vibration in open pit mines is a contributor to highwall damage, and failure of such walls can cause loss of reserves and interruptions to mine production. Poor stability and failure can be expensive, requiring recovery of ore by clean-up operations, modification of a mine plan, construction of new ramps, installation of extra ground support, and lost production during the remediation period. In underground mines, blast vibration can cause instability in large open stopes, caving operations and mine development tunnels.

It can therefore be desirable to measure vibrations in an attempt to determine whether an amount of vibration due to one or more events, e.g., blasting events, may lead to instability.

In existing systems and processes, vibrations in structures have typically been analysed based on measured motions of the particles in the structures, and subsequent determination of the peaks in velocity, acceleration or displacement of the particles, referred to as the peak particle velocity (PPV), the peak particle acceleration (PPA) or the peak particle displacement (PPD). Once determined, the PPV, PPA and/or PPD can be compared to preselected or predefined acceptable upper limits on peak velocity, acceleration or displacement to determine a likelihood of possible instability or damage in parts of the structure. These acceptable upper vibration velocity, acceleration and displacement limits are, however, difficult to determine accurately, appropriately and consistently, e.g., for each particular application or operation, and selecting incorrect PPV, PPA or PPD limits can be problematic. On the one hand, if the blast vibration limit (i.e., the preselected PPV, PPA or PPD limit) is too low, the cost of the operation can be unnecessarily high. On the other hand, if the vibration limit is too high, it can result in unsafe practices and undesirable damage to the natural structure (e.g., the rock or soil) and/or to other nearby structures including man-made structures.

Some existing systems and processes may use particle velocity to estimate deformation in a structure, such as strain in rock; however, the inventors have realised that these systems typically assume that the strain is linearly proportional to the particle velocity at a point, and thus may not be sufficient for estimating stress and strain in the vicinity (e.g., within a few vibration wavelengths, which can be referred to as being in the near field) of a vibration source (e.g., a blast point or focus) and/or due to relatively rapid transient events, e.g., blasting events.

The motions of the particles in the structure or structures can be related to each other through various forms of mechanical waves such as particle displacement, particle velocity, particle acceleration vibration waves, stress waves or strain waves propagating in the structure(s). The mechanical waves can also be referred to as motion waves.

Some existing systems and processes may use simple wave models (e.g., based on spherical, cylindrical and/or plane waves) to estimate propagation of the motion waves in structures (e.g., for plane waves it is based on a one-dimensional (1D) relationship between particle velocity and strain at each point); however, these simple models may be insufficient for determining the stress and strain caused by a relatively rapid event, such as a blast, and/or in the near field of the vibration source. Furthermore, for blasting, simple wave models may be unsuitable if blast holes are loaded with various different explosive types, if the explosives are delayed individually (i.e., they have different timing), or if the geology of the structure contains layers of different materials and/or other non-uniform structural or material zones. Non-uniformity in the structure (e.g., the blast medium) can cause propagating waves to be reflected, refracted, and transformed between modes, e.g., between waves in the medium and surface waves on the surface of the medium, and between waves of different types. The different types of waves include primary (P) waves (also referred to as compressional waves) whose particle motion is in the direction of propagation, secondary (S) waves (also referred to as shear waves) whose particle motion is perpendicular to the direction of propagation and which can have different polarisations, and surface waves such as Rayleigh (R) waves whose particle motion is elliptical, Love (L) waves and other waves that travel as guided waves.

It is desired to address or ameliorate one or more disadvantages or limitations associated with the prior art, or to at least provide a useful alternative.

SUMMARY

In accordance with the present invention there is provided a process for vibration analysis, including the steps of:
  receiving synchronized motion measurements of particle motion in two or three orthogonal dimensions over a selected period of time at a plurality of different measurement locations; and
  determining one or more strain waveforms in the orthogonal dimensions in regions spanning the plurality of measurement locations using the motion measurements.

The term "strain waveform" refers to a plurality of values of strain in a time sequence for each region. The orthogonal measurement dimensions can be the same as the orthogonal strain dimensions, or they can be related through a dimensional transformation.

In embodiments, the process can determine stress waveforms in the regions spanning the measurement locations, based on the strain waveforms and parameters of constitutive properties of a medium (e.g., a structure or a material) in the spanning regions.

The strain waveforms include strain values at each time instance in the selected period of time.

The spanning regions can be referred to as areas or volumes defined by cells, polygons or polyhedra, having vertices at the measurement locations, or areas or volumes within which measurement locations reside.

In embodiments, the motion measurements can be synchronized by various methods of synchronization including the use of timing signals received by monitors corresponding to the measurement locations from a shared or common source, e.g., a global positioning system (GPS) or an electronic timing reference circuit. Any mismatch in the synchronisation of the motion measurements limits the accuracy of the determined strain waveforms and this may be estimated based on the frequencies and wavelengths of the motion waves. For example, the present accuracy of GPS time synchronization may be in the range of a microsecond to several milliseconds, which may limit the determination of the strain waveforms to low frequencies and long wavelengths. The motion measurements can be synchronized with an expected event (e.g., a concussion or a blast with a plurality of blast holes) causing the particle motion such that the selected period of time provides a measurement duration that starts at or before any particle motion caused by the event, and lasts until after motion waves associated with the event have propagated beyond the measurement locations.

In embodiments, the process can include removing low-frequency artefacts from motion waveforms based on the motion measurements and/or knowledge of the frequency response of the ground. The motion waveforms represent the motion waves.

In embodiments, the process includes generating a two-dimensional (2D) or three-dimensional (3D) image of strain in an area or volume comprising the spanning regions (which corresponds to an area or volume between the measurement locations). Although the strain is defined strictly at a point (x,y,z), the process uses the point (x,y,z), and other surrounding points (x+dxi, y+dyi, z+dzi) to determine the average strain over the region spanning those points.

The measurement locations can be in the near field or the far field of the event, or in a transition zone between the near and far fields. The near field can refer to a region where the product of the wave number of the mechanical waveform and the distance to a point of interest is much greater than unity, the far field can refer to a region where the product of the wave number and the distance to a point of interest is much less than unity, and the transition zone can refer to a region in which the near field and the far field overlap and in which some near field effects may still be detected. Alternatively, or additionally, differentiation between the near field and the far field can be based on charge weight and distance: for example, a near-field blast vibration can have a charge weight scaled distance of less than 1 meter-per-square-root-kilogram (m/kg^0.5), whereas a far-field blast vibration can have a charge weight scaled distance of greater than 1 m/kg^0.5.

The motion measurements can include particle displacement, velocity and/or acceleration measurements made by motion sensors associated with the monitors. The motion measurements can be measured in the orthogonal dimensions. The motion sensors can include one or more geophones, accelerometers, and/or other devices that measure particle displacement, velocity or acceleration (e.g., non-contact transducers, blasting seismographs, or laser-based motion detectors, etc.). A measurement system may include a mixture of such devices (i.e., a plurality of the different types of the sensors).

The process can include determining displacement values at the measurement locations using the motion measurements.

The process can include determining strain values in the strain waveforms using displacement gradients or strain components between the measurement locations based on the respective displacement values.

The process can include solving relationships between: the displacement gradients or the strain components; and at least three non-collinear ones of the measurement locations for 2D regions, or at least four non-coplanar ones of the measurement locations for 3D regions.

The process can include simultaneously solving more than three independent equations for 2D regions, or simultaneously solving more than six independent equations for 3D regions, to determine the strain values.

The process can include solving the equations (subject to appropriate boundary conditions) using a matrix solution method, e.g., including a singular value decomposition process.

The relationships can include linear relationships between:
(i) coordinate values of selected ones of the measurement locations;
(ii) the displacement values of the selected measurement locations; and
(iii) the displacement gradients in the regions spanning the selected measurement locations.

The relationships can include linear relationships between:
(i) coordinate values of selected ones of the measurement locations;
(ii) the displacement values of the selected measurement locations;
(iii) the displacement gradients in the regions spanning the selected measurement locations; and
(iv) rotations of the regions spanning the selected measurement locations.

The relationships can include linear relationships between: (i) elongations of vectors between selected ones of the measurement locations; (ii) the displacement gradients in the regions spanning the selected measurement locations; and (iii) direction cosines of the vectors.

The relationships can include linear relationships between: (i) angular changes of vectors between selected ones of the measurement locations; (ii) the displacement gradients in the regions spanning the selected measurement locations; and (iii) direction cosines of the vectors.

In embodiments, the process includes selecting parameters for making the motion measurements, including any one or more of the following steps:
  selecting a spacing of the measurement locations (e.g., based on frequencies and speeds of the strain waveforms);
  selecting a sampling rate for the motion measurements (e.g., based on the frequencies and the speeds of the strain waveforms); and
  selecting a sampling duration based on the selected period of time.

The present invention also provides a process for vibration analysis, including the steps of:
  receiving motion data representing synchronised motion measurements of particle motion at a plurality of measurement locations;
  selecting three or more non-collinear ones of the measurement locations; and
  generating, using the motion measurements, strain data representing at least one two-dimensional strain value in at least one region spanning the three or more non-collinear measurement locations.

The present invention also provides a process for vibration analysis, including the steps of:
  receiving motion data representing synchronised motion measurements of particle motion at a plurality of measurement locations;
  selecting four or more non-coplanar ones of the measurement locations; and generating, using the motion measurements, strain data representing at least one three-dimensional strain value in at least one region spanning the four or more non-coplanar measurement locations.

The strain value can be a normal strain value, or a shear strain value, which is a tensorial component that may be represented by a plurality of vectorial components (e.g., in a Cartesian or curvilinear coordinate system).

In embodiments, the step of generating the strain data includes the step of determining strain components of the strain value using vector components of the motion measurements.

In embodiments, the step of generating the strain data can include the steps of:
  determining at least one displacement gradient in the region using the motion measurements and spacings between the measurement locations; and
  determining the strain value using the at least one displacement gradient.

In embodiments, the particle motion is linear motion or angular motion.

The present invention also provides an analysis system including modules configured to perform any one or more of the processes described above.

The present invention also provides a system for vibration analysis, including an analysis system configured to perform any one or more of the processes described above.

The present invention also provides computer-readable storage media, including one or more modules configured to perform any one or more of the processes described above.

The present invention also provides a process for vibration analysis, including the steps of:
  receiving synchronized motion measurements of particles displaced by a blast in two or three orthogonal dimensions, over a selected period of time after the blast, and at a plurality of respective measurement locations, wherein the motion measurements represent relative displacements; and
  determining a plurality of strain waveforms in the orthogonal dimensions in a plurality of respective regions using:
    the motion measurements,
    data representing the measurement locations, and
    a predetermined relationship between strain in each region, relative locations of ones of the particles surrounding each region, and infinitesimal movements of the ones of the particles.

The strain waveforms can include normal and shear strain waveforms.

The motion measurements can include elongations, rotations or their combination between the particles.

The selected period of time can include time during the blast.

The present invention also provides a system for vibration analysis including:
  an input module configured to receive synchronized motion measurements of particles displaced by a blast in two or three orthogonal dimensions, over a selected period of time after the blast, and at a plurality of respective measurement locations, wherein the motion measurements represent relative displacements; and
  a processing module configured to determine a plurality of strain waveforms in the orthogonal dimensions in a plurality of respective regions using:
    the motion measurements;
    data representing the measurement locations, and
    a predetermined relationship between strain in each region, relative locations of ones of the particles surrounding each region, and infinitesimal movements of the ones of the particles.

The present invention also provides a system for vibration analysis of blasting, including:
  a plurality of sensors configured to generate synchronised motion measurements representing displacements at respective measurement locations in a medium due to vibration waves caused by at least one blasting event;
  a measurement hub configured to receive signals representing the motion measurements from the sensors over a selected period of time after the event; and
  at least one processing module configured to generate, based on the synchronised motion measurements and the measurement locations, strain data representing strain in at least one region spanning the measurement locations.

The measurement locations can be non-collinear, the synchronised motion measurements can represent displacements in two orthogonal directions, and the processing module can be configured to generate the strain data in two orthogonal directions.

The measurement locations can be non-coplanar, the synchronised motion measurements can represent displacements in three orthogonal directions, and the processing module can be configured to generate the strain data in three orthogonal directions.

The plurality of measurement locations can include a plurality of groups of the measurement locations, and the processing module can be configured to generate strain data representing strain in a region spanning each group.

The measurement locations in each group can be non-collinear, the synchronised motion measurements can represent displacements in two orthogonal directions, and the processing module can be configured to generate the strain waveforms in two orthogonal directions.

The measurement locations in each group can be non-coplanar, the synchronised motion measurements can represent displacements in three orthogonal directions, and the processing module can be configured to generate the strain waveforms in three orthogonal directions.

The plurality of strain waveforms can be generated using at least one predetermined relationship between strain in a region spanning the measurement locations, relative locations of the measurement locations, and infinitesimal movement of the particles.

The medium can include at least one structure and/or geological material.

The system can include at least one blasting and/or impact apparatus configured to initiate the blasting event.

The present invention also provides a process for vibration analysis of blasting, including the steps of:
  generating synchronised motion measurements representing displacements at respective measurement locations in a medium due to vibration waves caused by at least one blasting event;
  receiving signals representing the motion measurements from the sensors over a selected period of time after the event; and
  at least one processing module configured to generate, based on the synchronised motion measurements and the measurement locations, strain data representing strain in at least one region spanning the measurement locations.

BRIEF DESCRIPTION OF THE DRAWINGS

Preferred embodiments of the present invention are hereinafter further described, by way of non-limiting example only, with reference to the accompanying drawings, in which.

DETAILED DESCRIPTION

System 100

Figure 1:
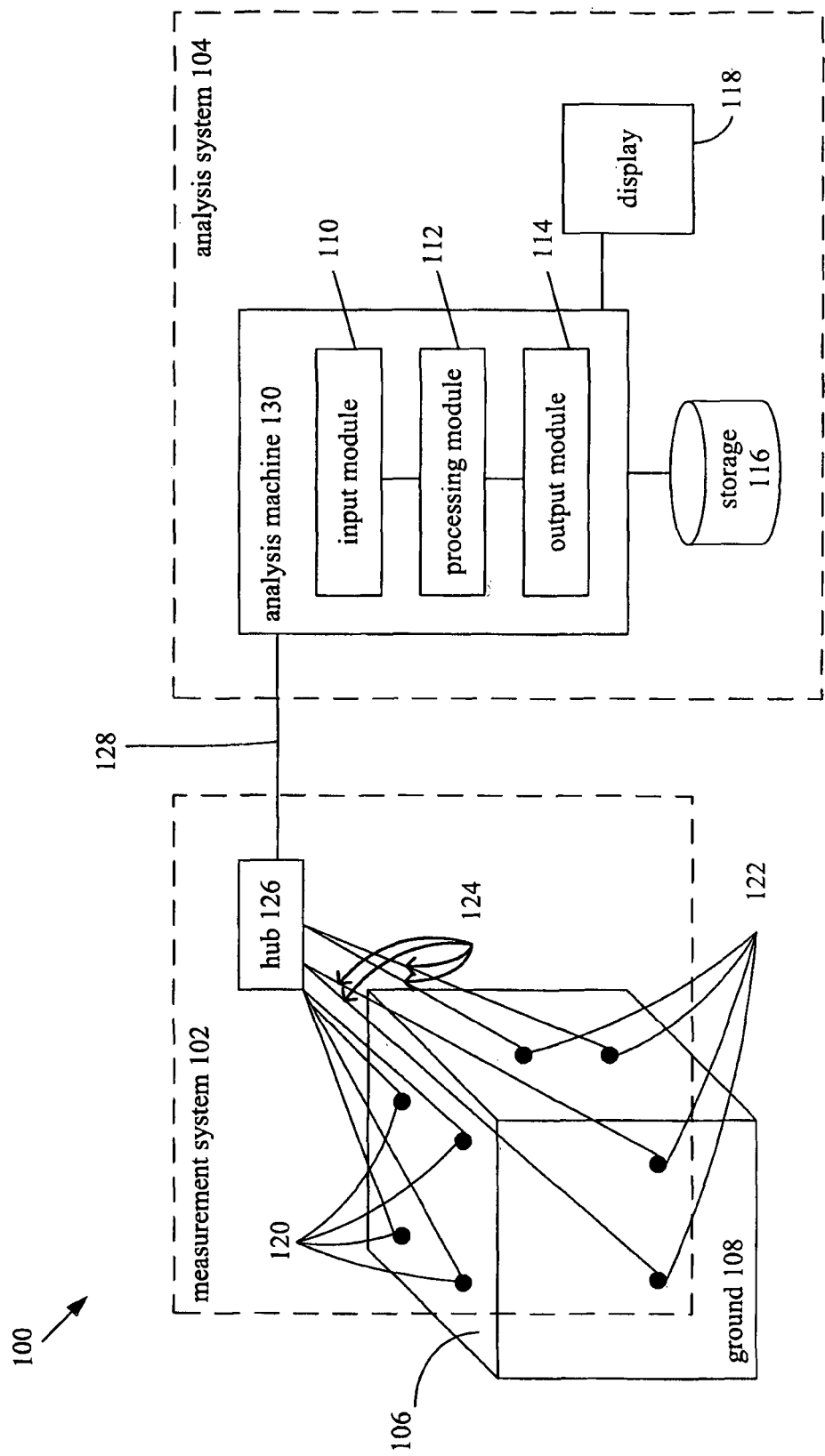
FIG. 1 is a block diagram of a system for measurement and analysis.

A system 100 for vibration analysis, as shown in FIG. 1, includes a measurement system 102 for measuring particle motions (or movements) including particle vibrations, and an analysis system 104 for determining strain waveforms based on the measured particle motions.

The system 100 uses synchronized measurements of the dynamic motion (such as displacements, velocity, or acceleration) of at least one particle to determine two-dimensional (2D) or three-dimensional (3D) estimates of dynamic strain in at least one region spanning a group of particles, including values of strain in the form of dynamic strain tensors.

The particle motions are measured by motion sensors associated with monitors distributed in a medium. The medium can include component materials or sub-structures, e.g., different geological formations or different portions of a man-made structure. The medium can include natural and/or man-made structures, e.g., the medium can include the earth or the ground, such as ground 108 (below a ground surface 106), as shown in FIG. 1. The surface 106 can be the surface of a mining site, a construction site, or a geo-exploration site.

The particle motions are due to ground vibrations (including shock waves) caused by one or more man-made events, such as impacts from pile driving in civil construction, mechanical shakers and blasting, e.g., in mining, quarrying, construction, or seismic exploration for minerals, oil, gas and other sub-surface deposits. The vibrations can be caused by a plurality of sources, e.g., in a mining application, there can be a plurality of blasts in respective blast holes with different blast locations and blast timings for a production blast. Example explosive sources can include charges with masses from a few grams to several hundred tonnes with length scales from a few millimetres ta a hundred metres or more. The charges may be deployed in a range of arrangements or dispositions ranging from vertical to horizontal, depending on the industrial application (e.g., mining, quarrying or exploration). The types of charges can be black powder, packaged explosives, bulk explosives and include primary, secondary and tertiary explosives initiated using a variety of detonators or fuses including pyrotechnic, electric, electronic delay detonators or exploding bridgewires, laser initiation and combinations of these. For demolition applications, including demolition of buildings, example explosive sources can include similar charges to those used in mining and also specialised charges with specific shapes to produce the desired effects of breaking, cutting or removing physical constraints of the building or structure in a controlled manner.

The particle motions are caused directly by the impact (e.g., a blast), or indirectly e.g., by motion waves or vibration waves (e.g., strain or stress waves) initiated by the impact propagating in or through a medium. The motion waves start at the sources and propagate through the medium in patterns that are caused, determined or controlled by the properties of the medium, including the refractive indices of its components (e.g., the rock types in the medium) and interfaces between components (e.g., interfaces between different rock types, and edges or boundaries of material domains). Typical motion wave speeds in rock and soils vary between several hundred metres per second to several thousand metres per second. In other materials, e.g., solid state materials such as mixtures, dielectrics, metals and semiconductors, etc., a similar range of motion wave speeds apply and these are affected by the condition of the material including the presence of dislocations, grains, joints, dykes, cracks, pores, fluids and other single or multiple imperfections that may be distributed uniformly and/or non-uniformly.

The determined dynamic strain in each region can be used to estimate and evaluate damage or potential damage caused by the particle motions against various strength or other failure criteria of the medium, in that region e.g., using a tensile or a Mohr-Coulomb failure criterion for ground or rock in the medium. Cumulative effects of the particle motions can be determined using principles of material science, e.g., the effects of a plurality of blast vibrations on rock structures can be determined based on known limits for particular materials and particular operations including tunnelling, construction, quarries, sub-surface exploration, and surface and underground mining.

Based on the determined strains in a plurality of regions, the system 100 can determine planes of principal strains, maximum shear strains, or strain states, and thus the particle motion waves can be related to known features of the medium, e.g., to fault planes or weak joints of geology in a blasting site or interpreted in relation to effects from particular rock structures. The determined dynamic strain can be related more directly to rock mechanics and material strengths than the peak particle velocity (PPV) or peak particle acceleration (PPA), thus determination of the dynamic strain from blast vibrations may improve quantification of blast damage and selection of a blast vibration limit for critical structures, e.g., in mining, exploration, or construction.

Measurement System 102

The measurement system 102 includes a plurality of the monitors (also referred to as detectors) including motion sensors at a plurality of respective different measurement locations in the medium. The monitors are configured to measure, the measurement locations of their respective motion sensors, mechanical motion of adjacent particles (i.e., particles respectively adjacent to the monitors), or measurement of virtual particles formed by the monitors, in the medium due to the motion waves. The measurement system 102 performs a measurement process 600, described in detail below.

Each motion sensor can be embedded in the medium (e.g., as embedded monitors 122, which are placed or embedded in the ground 108, as shown in FIG. 1), or can be located on or adjacent to the surface of the medium (e.g., as surface monitors 120, which are placed or arrayed on the surface 106 of the ground 108, as shown in FIG. 1).

The motion of the medium at each measurement location is referred to as "particle motion" because it is associated with motion of the particles or the virtual particles in the medium at that location relative to other particles in the medium. The term "particles" can also refer to the motion sensors or the monitors themselves because they are generally significantly smaller than the wavelengths of the motion waveforms, e.g., the monitors can be less than about 100 mm long in each dimension, and a typical wavelength for an underground blast in hard rock is more than about 2.0 m.

Each monitor detects and measures motion of the medium at the measurement location of its motion sensors in two or three orthogonal dimensions, e.g., in two or three Cartesian directions, thus generating bi-axial/two-dimensional (2D) measurements, or triaxial/three-dimensional (3D) measurements, of the particle motion. The number of orthogonal measurement axes of each monitor is selected to be two or three depending on whether 2D or 3D measurements are required, although it is usual to have 3D measurements even for a 2D interpretation.

Motion at each measurement location can be used to determine rotation of the region of the medium spanning a group of the measurement locations, i.e., rotation of the region can be measured using multiple monitors.

Figure 2:
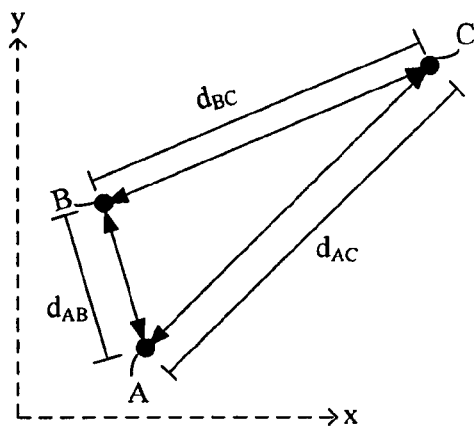
FIG. 2 is a diagram of three monitoring points of the system spanning a two-dimensional measurement region.
Figure 3:
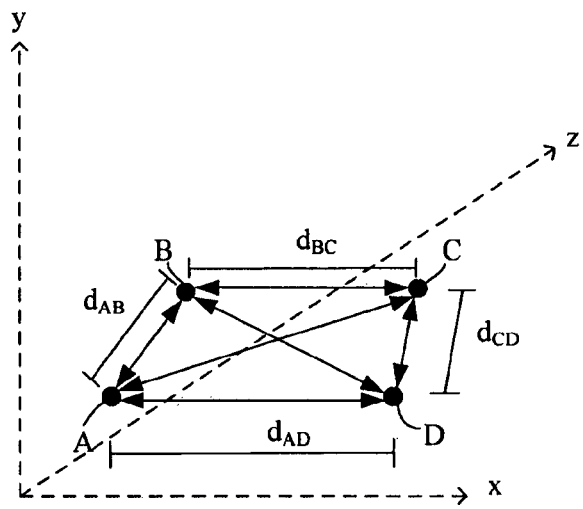
FIG. 3 is a diagram of four monitoring points of the system spanning a three-dimensional measurement region.

If the measurement locations or monitoring points are arranged in a 2D plane, e.g., as the surface monitors 120, or if only three measurement locations are used, the motion waveforms can only be estimated in two dimensions. If four non-coplanar measurement locations are used, the motion waveforms can be estimated in three dimensions. The measurement locations must be substantially non-collinear in the two dimensions, or non-coplanar in the three dimensions, to allow estimation of the waveforms in two or three dimensions respectively. Accordingly, a minimum of three sensors are arranged non-collinearly in the medium at points A, B and C at the vertices of a triangle, as shown in FIG. 2) for motion estimation in a 2D measurement region. Similarly, a minimum of four sensors are arranged non-coplanarly in the medium (e.g., at points A, B, C and D at the vertices of a pyramid, as shown in FIG. 3) for motion estimation in a 3D measurement region. Using additional non-collinear or non-coplanar monitoring points (so-called "redundant" monitoring points, i.e., more than three for 2D and more than four for 3D) can reduce the effects of measurement error/noise and can increase the number of measurement regions thus increasing the total coverage, or the spatial resolution of the estimated strain waveforms. Additional monitoring points can be used to determine rotations in the region of interest spanned by the monitoring points. Additional monitoring points can also be used to estimate the gradients based on higher-order relationships between displacements and displacement gradients, e.g., as shown in Equation (7A) hereinafter.

The monitors are spatially coordinated in that their motion measurements are recorded with reference to coordinate values of each monitoring point in a common or shared spatial coordinate system (e.g., using a 2D or 3D locator or survey tool, such as an assisted GPS system). Thus the 2D or 3D position/location of each monitoring point (and thus the location associated with each motion measurement) is selected and/or recorded during the monitoring process. Generally the monitors are devices that contain or include the motion sensors (e.g., the accelerometers) for measuring the particle motion at the measurement locations; however, in some embodiments, the monitors can include separate motion sensors e.g., that are in communication with the monitor using electrical, optical or wireless connections, and in this case the sensors define the measurement locations or monitoring points because the particle motions are being measured at the sensor locations.

The arrangement of the monitoring points in the medium determines the spatial resolution for the strain estimates. Accordingly, the monitoring points are placed in the medium with a selected spacing, with the selection based on the required resolution of the strain waveform estimates. The process of selecting these spacings is part of the measurement process 600, described below. Spacings between adjacent measurement locations in the propagation directions of the motion waves are selected to be sufficiently close to avoid aliasing: accordingly, the measurement locations are spaced at less than half the distance of the shortest expected wavelength of the motion waves. For example, for measuring dynamic strain (e.g., the maximum and minimum strain) between two points, monitoring the spacing between the two points should be less than a quarter of the wavelength to achieve at least a 90% accuracy of the measurement for the frequency component corresponding to that wavelength. Similarly, the sampling rate of the measurements is selected to be more than twice the frequency of the highest expected frequency of the motion waves. Incorrect sampling in space and time may lead in the worst case to aliasing of the desired motion recordings. In the measurement process 600, the resolutions in space and time are selected to be sufficiently small to avoid or at least inhibit signal aliasing, and thus to ensure sufficient sampling of the strain waveforms in space and time. In the case of spatial sampling, the following are selected: (i) the spacings between the motion sensors, and (ii) the orientations of the motion sensors with respect to the expected direction of strain wave propagation and the expected maximum frequency in the strain wave.

The spacings between the measurement locations, and the sampling periods of the motion measurements, are selected based on the following relationships:

$$\Delta x \le \frac{\lambda_{min}}{2},$$

and $$\Delta T \le \frac{1}{2 f_{max}},$$

where $$c_x = \lambda_{min} f_{max},$$

and $\Delta x$ is the distance between two monitoring points in one of the orthogonal directions (e.g., the x-direction), $\lambda_{min}$ is the expected minimum wavelength in the motion waves (e.g., the strain wave), $\Delta T$ is the temporal sample interval (or the sampling period), $f_{max}$ is the expected maximum frequency in the strain wave, and $c_x$ is the apparent velocity of the strain wave in the x-direction. Equivalent relationships are used to select the distances between the measurement locations in the other orthogonal directions: the y-direction and the z-direction. An alternative is to use the apparent wavelength in the line or direction joining the source of the vibration to the monitor and the associated apparent velocity in that direction.

The 2D or 3D orientation of each motion sensor is also selected and/or recorded during the monitoring process (e.g., using a compass and/or a levelling tool). Each motion sensor (e.g., in a monitor) can be placed in a known orientation so that the results may be aligned within a site-wide coordinate system through coordinate transformation of the recorded tri-axial vibration components. These transformations use standard geometric manipulation of vectors in 3D space. Typically, the alignment of the tri-axial motion sensors uses a horizontal alignment e.g., by compass bearing of the two horizontal motion sensors and a bubble level for alignment of the vertical motion sensor. Alignment errors can be less than one degree using these procedures. Alternative alignment techniques that offer better accuracy may be used.

The sampling rates of the monitors are determined as the inverse of the sampling periods.

The sampling rate of the monitors is generally the same for all monitors in the measurement system 102. The sampling rate determines the temporal resolution of the estimated waveforms, thus the sampling rate is selected based on the required temporal resolution of the strain waveforms, as described above.

Operational characteristics of the monitors, including their sampling rates, measurement accuracies and frequency response, are selected in the measurement process 600, as described below.

The measurement resolution or measurement accuracy of the monitors and their sensors' locations determines the final accuracy or resolution of the estimated waveforms, thus the monitor accuracy is selected based on the required final accuracy.

The frequency response of the monitors determines the range of frequencies available in the measured waveform, and thus in the strain waveforms.

The monitors may be commercially available vibration monitors. In an example, the monitors can be time-synchronized vibration monitors, e.g., including accelerometers or tri-axial geophones from ESG Solutions (Kingston, Ontario, Canada, www.esgsolutions.com). The units can be synchronized by the data acquisition system to within a few microseconds. Other types of data acquisition devices may be Kelunji Echo monitors or Instantel Blastmates using in-built clocks or GPS signals to synchronize the measurements.

The monitors measure their respective local particle motions over a selected sampling duration (T), and then transmit these motion measurements, as signals and/or data, over a plurality of communications links 124 which connect the surface monitors 120 and the embedded monitors 122 to a hub 126, as shown in FIG. 1. The communication links 124 between the monitors and the hub 126 can be wired, or optical, or wireless connections, depending on the type of monitors and hub used in the system 100. Current commercially available monitors can store or transmit their recorded data for post-processing; alternatively, the monitors may perform real-time processing to perform at least a portion of the measurement process 600 and the analysis process 700 to produce the desired strain waveforms. The hub 126 can be a computer-based system or an integrated data acquisition system that stores all the desired measured motions (e.g., including an eDAQ data recorder such as an eDAQ-LITE SoMat recorder from Hottinger Baldwin Messtechnik GmbH (HBM), Germany).

The motion measurements are synchronized by synchronizing the recording of the motion measurements by the monitors with reference to a common time base or reference. A high degree of time synchronization is generally required. The accuracy required in the time synchronization of the measurements is based on: (i) the spatial arrangement of the monitors; and (ii) the frequency content and wavelengths of the waves. The frequency content and wavelengths of the waves are related by the speed of the wave propagation in the medium, e.g., in the rock or soil in the ground 108. For example, a synchronization error of about 45 µs or less (e.g., from monitors coordinated using GPS signals) may be acceptable for strain waves with frequencies below 50 Hz, but not for higher frequencies, whereas a synchronization error of about 0.45 µs or less (e.g., from an eDAQ system) may be acceptable for strain wave frequencies up to about 3000 Hz.

The hub 126 receives and records the motion measurements from the monitors, and sends the motion measurements, as signals and/or data, to, the analysis system 104 via a communication connection 128 between the hub 126 and the analysis system 104. The connection 128 can be a wired connection, an optical connection or a wireless connection, e.g., in a monitoring station or a mining site; alternatively, the connection 128 can represent the transfer of stored signals or data, e.g., stored on a removal computer-readable memory (e.g., a disk or memory stick), or transferred as a data file via the Internet.

Alternatively, the monitors can record the motion waveforms individually, and then transfer their recorded waveforms to the analysis system 104 after they have been physically gathered from the medium. The storage can be computer-readable storage, such as flash memory, and the storage can be accessed using an electronic connection to the hub 126; or the storage can be in the form of a removable card that is readable directly by the analysis machine 130.

In an example measurement system, five synchronized vibration monitors can be arranged in the ground around a source point of interest. The speed of propagation of the strain wave (e.g., a P wave) in the ground can be about 4000 metres per second (m/s). For an expected maximum frequency in the strain wave of 1000 Hz, the spatial and temporal sampling criteria to avoid aliasing are selected as follows: the minimum sample interval $\Delta T_{min}$ must be $1/(2*1000)=0.5$ milliseconds; and the maximum monitor spacing $\Delta x_{max}$ must be $4000/(2*1000)=2$ metres. Thus the monitors are spaced closer than 2 metres along the expected direction of propagation of the wave, and the data acquisition system samples at faster than 0.5 milliseconds per data point, to sample the strain wave without aliasing. It is usual to select a density and rate better than the minimum required to avoid aliasing, thus enabling greater sampling both spatially and temporally. For example, data acquisition systems can usually sample at higher rates than that demanded in the example above with high measurement amplitude resolution (16 bits or 24 bits).

The locations of the monitors are also selected based on the expected direction that the strain wave will propagate. Typically, the monitors are placed approximately in the direction of propagation of the strain wave.

Analysis System 104

The analysis system 104 includes an analysis machine 130, e.g., a personal computer (PC) or computer server, which includes the following, as shown in FIG. 1:

(i) an input module 110 configured to receive the motion measurements from the monitors;

(ii) a processing module 112 configured to determine the strain waveforms in the two or three orthogonal dimensions in the regions spanned by the plurality of monitors using the motion measurements; and (iii) an output module 114 configured to send the strain waveforms (and/or stress waveforms) to storage (e.g., to storage 116 in the system 100) and/or to a display 118 connected to the analysis machine 130, e.g., for display to a user such as a geologist or structural engineer monitoring the medium, e.g., for damage.

The analysis system. 104 executes or performs an analysis process 700, described in detail below, using the modules 110, 112 and 114.

The analysis machine 130 can include commercially available modelling modules 503, which provide waveform superposition models including a Multi-Seed-Waveform (MSW) model or a statistical Monte Carlo vibration model. The determined strain waveforms can be displayed and compared to outputs of the modelling modules 503, such as predicted blast vibration particle velocity or acceleration waveforms produced by the MSW blast vibration model and Monte Carlo model. The MSW and Monte Carlo models can generate virtual motion measurements (e.g., virtual vibration waveforms) at virtual monitor locations. Instead of using the measured motion data, the modelling modules 503 can provide the virtual motion data for generating virtual dynamic strain values in regions spanned by virtual locations corresponding to the virtual motions (e.g., displacement waveforms) in the analysis process 700. The analysis process 700 may be applied to data from any model that generates the required input motion waveforms of particle displacement, velocity or acceleration from which the dynamic strains may be derived. Interpolation and extrapolation techniques may be used to extend the data in regions where they are not measured but they may be inferred.

Measurement Process 600

In the measurement process 600, the measurement system 102 is configured based on the required characteristics of the strain estimates, and then activated to measure (or equivalently, sense or detect) the particle motions at the measurement locations (using the monitors), and transmit this information to the analysis system 104.

Figure 6:
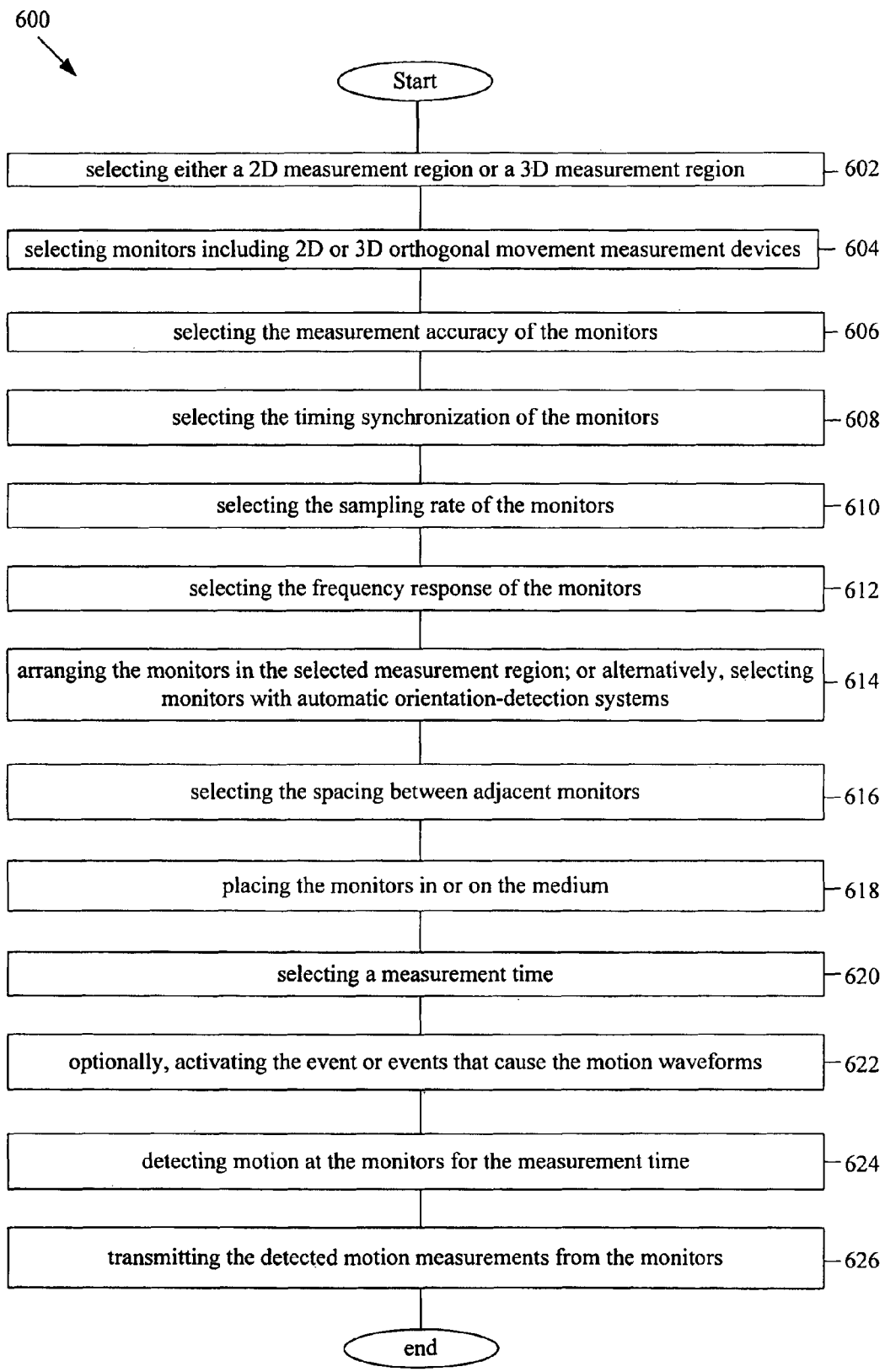
FIG. 6 is a flow diagram of a measurement process performed by the system.

As shown in FIG. 6, the measurement process 600 includes the following steps:

1. selecting either a 2D measurement region for making 2D measurements, e.g., on the surface 106, or a 3D measurement region for making 3D measurements, e.g., in the ground 108 (step 602);
2. selecting monitors including 2D or 3D orthogonal motion sensors, e.g., detectors with bi-axial or tri-axial accelerometers, based on whether the measurement region is 2D or 3D (although triaxial sensors may be used for a 2D measurement region) (step 604);
3. selecting the measurement accuracy (also referred to as the "resolution") of the sensors in the monitors based on the required accuracy of the strain waveforms, e.g., for a required maximum strain waveform error of 5%, the measurement accuracy of the sensors is determined on the basis of the likely frequencies in the strain wave; this may be guided by numerical modelling to examine the errors produced in the estimated strain waveforms for different configurations of monitors and their orientation with respect to the source of the strain wave (step 606);
4. selecting the timing synchronization of the monitors to have selected accuracy corresponding to the required timing accuracy of the strain waveforms, e.g., the timing accuracy can be selected based on the sampling criteria described above (step 608);
5. selecting the sampling rate ($1/\Delta T$) of the monitors to correspond to the required sampling rate of the dynamic strain waveforms, based on the sampling period described above (step 610);
6. selecting the frequency response of the monitors and/or sensors to correspond to the required range of frequencies expected in the strain waveforms, e.g., most far-field ground vibrations are in the range of about 5 Hz to 250 Hz for surface blasts and about 5 Hz to 1000 Hz for surface measurements of underground or tunnel blasts; however for near-field monitoring the maximum frequencies can be as much as 5000 Hz or higher for small sources recorded by monitors located very close to them, thus it may be required to conduct preliminary measurements to determine the upper frequencies in any given situation and establish the sampling criteria and measurement locations appropriately to ensure adequate sampling using the criteria described above (step 612);
7. selecting the orientations of the monitors in the selected measurement region such that motion in each required orthogonal direction is measured with respect to the same direction by all of the monitors or alternatively, selecting monitors with automatic orientation-detection systems, e.g., gyroscopes, to ensure that motion in each direction is measured in that direction by the monitors, for example, accuracies of monitor orientation within one degree may be sufficient to adequately produce reliable strain wave estimates (step 614);
8. selecting the spacings (e.g., $\Delta x$, $\Delta y$, and $\Delta z$) between adjacent measurement locations to correspond to the required spatial resolution of the strain waveform estimates (at least in the expected directions of propagation of the motion waves), guided by any background measurements or specific site knowledge and the spacing requirements described above (step 616);
9. placing or arranging the monitors, and/or sensors in or on the medium in accordance with the selected 2D or 3D measurement region, the selected orientations and spacings, and the expected direction of propagation of the waves of interest (step 618);
10. selecting a measurement time or the expected impact time (e.g., a blast time) and duration during which the monitors will record motion measurements based on the expected duration of the strain waveforms, e.g., in a quarry blast the waveforms will be several seconds long (step 620);
11. activating the event or events that cause the motion waveforms, e.g., activating blasts in a mining site (step 622);
12. detecting particle motion at the measurement locations for the measurement duration, which can include detecting displacement vectors, velocity vectors, acceleration vectors, etc. using the motion sensors (step 624); and
13. transmitting the detected motion measurements from the monitors via the links 124 to the hub 126, either periodically, continuously, or at a selected time after each event or events (step 626).

To generate a non-zero strain waveform for a region, at least one monitor of the group spanned by the region detects a motion waveform with its sensors, i.e., stress and strain estimates can be generated based on the movement of only one sensor for each region provided the above anti-aliasing requirements are met.

Analysis Process 700

The motion measurements from the measurement process 600 are associated with a dynamic displacement vector at each measurement location (generally corresponding to each monitor). These displacements (or in a modelling process, the virtual displacements described above) can be used directly to determine strains in regions between, or spanning, the measurement locations (using the displacements corresponding to the plurality of measurement locations). Alternatively, the displacements can be used to determine elongations or rotations of the regions between the measurement locations, and these elongations or rotations can also be used to estimate the strains in the regions.

In the analysis process, the analysis system 104 determines normal and shear strain waveforms based on the measured motion waveforms from the measurement system 102.

Figure 4:
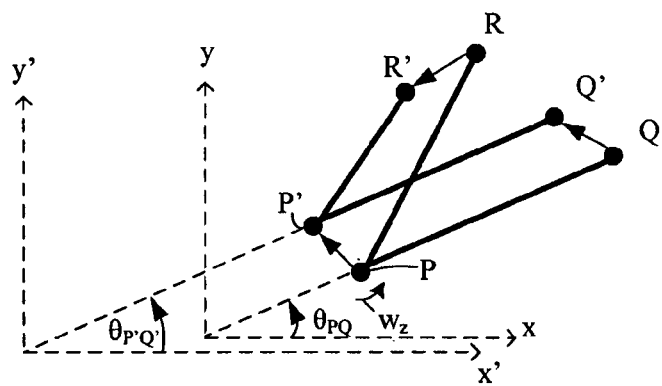
FIG. 4 is a diagram of three monitoring points of the system being displaced.
Figure 7:
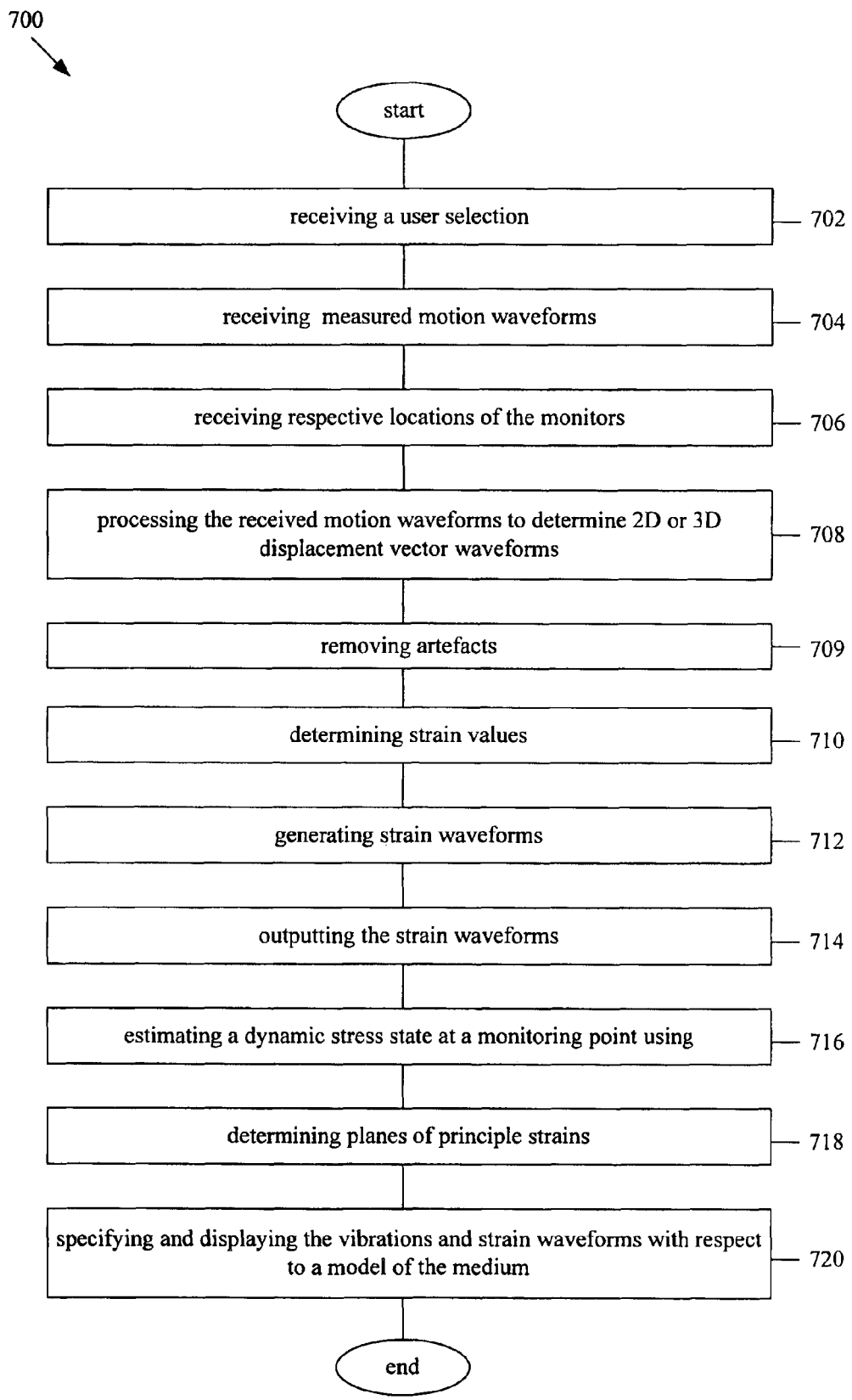
FIG. 7 is a flow diagram of an analysis process performed by the system.

As shown in FIG. 7, the analysis process 700 includes the following steps:

1. receiving a user selection, e.g., using the keyboard/mouse 518, indicating which of the following analysis processes is to be used: a pure displacements analysis process, a displacements and rotations analysis process, an elongations analysis process, an angles analysis process, or a mixed data analysis process; or alternatively, the particular type of analysis process can be pre-selected as a default by the processing module 112 (step 702);
2. receiving signals and/or data by the input module 110 from the measurement system 102 representing, or from the modelling modules 503, the motion measurements (step 704);
3. receiving, by the input module 110, signals and/or data representing the respective measurement locations, e.g., associated with the monitors, sensors or virtual locations, which can be represented as coordinate values (e.g., x and y in 2D, or x, y and z in 3D) on a coordinate system (e.g., a'selected Cartesian system) for each point (e.g., for the points P, Q and R on the 2D x-y system shown in FIG. 4) (step 706);
4. processing the received motion measurements to determine 2D or 3D displacement value vector waveforms over the measurement time for the respective measurement locations, which may include direct measurement of the displacements or integrating values in the motion waveforms representing velocities, accelerations etc., to determine the displacement vector values for each sampling time in the measured motion waveforms (and thus determining displacement waveforms), and if necessary transforming location and displacement values from the coordinate axes of the monitors (i.e., the measurement dimensions or directions) to the coordinate axes selected for determining the strain (i.e., the strain dimensions or directions) using one or more standard geometric transformations: for example, the displacement vector for each monitoring point can be represented as s, which includes three mutually orthogonal displacements u, v and w at each point, e.g., at the points P, Q and R, shown in FIG. 4 (step 708);
5. removing low-frequency artefacts from the displacement waveforms by filtering out or substantially attenuating (e.g., using a digital filter) all frequencies below the a selected high pass frequency limit, e.g., 1 Hz; alternatively, this filter can be applied to the received motion waveforms before step 708 (step 709);
6. determining, by the processing module 112, strain values in at least one region spanning the measurement locations, for the points in time corresponding to the synchronized sampling times in the measurement time, by processing the displacement values (in vector waveforms) and the measurement locations values, using the selected one of the analysis processes (selected in step 702), and thus generating corresponding average strain values in respective regions spanned by selected ones of the measurement locations for each of the points in time (step 710);
7. generating strain waveforms in at least one region spanning the measurement locations by concatenating the generated strain values at consecutive ones of the time points from data at the respective locations over the sampling duration (step 712);
8. outputting the strain values, by the output module 114, to the storage 116, or to the display 118, using corresponding electronic signals and/or digital data (step 714);
9. generating stress values (associated with dynamic stress states) of the regions using the strain values and standard constitutive relationships, e.g., Hooke's law or equivalents, associated with the medium, e.g., based on rock properties (step 716);
10. determining (for each time instance in the measured duration) planes of principal' strains or stresses, directional cosines of the planes of principal strain, maximum shear strains, or strain states at particular planes, based on the strain values (step 718); and
11. specifying and displaying the vibration values strain values with respect to a model of the medium, e.g., at a fault plane or at weak joints in a blasting site (step 720).

Once a network of monitors is deployed (or built into a measurement region, such as an area or a volume of interest) the strain values may be generated and displayed in real time to a person monitoring the measurement region, e.g., for assessing damage in the medium.

The analysis system 104 can use various combinations of the synchronised displacement values at the respective locations to generate maps of the strain waveforms over time and at different resolutions, depending on the density of selected measurement locations and the time sampling. For example, a first set of strain values can use displacement values from a first group including directly adjacent measurement locations, and a second set of strain values can use displacement values from a second group including non-adjacent (and thus more widely spaced) measurement locations: in this case, the second set of strain values would be associated with average strains over a larger region compared to the first set of strain values.

The analysis process 700 can be repeated continuously, or periodically, when each time sample of the motion waveforms is captured, or it can process the motion waveforms after they have been wholly recorded by the measurement system 102, e.g., after a blasting event.

The measurement locations received in step 706 are preferably the pre-movement sensor positions (rather than the post-movement sensor positions), because the site survey typically occurs pre-movement (particularly for near-field locations). Furthermore, the pre-movement marker positions can be consistent with Euler coordinate systems, which may be commonly used in dynamic analysis theory. Nevertheless the post-movement sensor locations may be used in some embodiments.

Generating the displacement waveforms in step 708 can include integrating measurements of particle velocity or acceleration either by standard integration with respect to time, or perhaps more efficiently by transformation of the recorded data into the frequency domain and using standard division by frequency that performs the integration and then transforming the result back into the time domain.

The artefacts in the lower frequencies are removed in step 709 by appropriate filtering methods that can include zero-phase digital filtering, or by curve fitting low-order polynomials to the integrated waveforms and removing the polynomial trend, or by other adaptive filtering methods depending on the presence of artefacts arising from the integration process. These artefacts can arise due to low-frequency content in the measured motion waves that are not due to actual motion of the medium but have been introduced due to other extraneous causes such as the limitations of the electronics in the measurement system.

Determining the strain values in step 710 includes determining: normal strain in 2D (represented by the orthogonal x and y components $\in_x$ and $\in_y$), or in 3D (represented by the orthogonal x, y and z components $\in_x$, $\in_y$ and $\in_z$); and shear strain in 2D (represented by component $\in_{xy}$), or in 3D (represented by the orthogonal components $\in_{xy}$, $\in_{yz}$ and $\in_{zx}$).

The processing module 112 determines (or estimates) the normal and shear strain values using relationships between: (i) the strain in a region; (ii) relative locations of the particles in the group spanned by that region; and (iii) infinitesimal displacement of these particles. These relationships can use displacement gradients. In 2D, the normal strains $\in_x$ and $\in_y$ are determined based on respective partial derivatives of the displacements, along their respective parallel axes based on the relationships in Equations (1) and (2), and the shear strain $\in_{xy}$ is determined based on partial derivations of the displacements along their respective orthogonal axes, based on the relationship in Equation (3):

$$\varepsilon_x = \frac{\partial u}{\partial x}, \tag{1}$$

$$\varepsilon_y = \frac{\partial v}{\partial y}, \tag{2}$$

$$\varepsilon_{xy} = \frac{1}{2}\left(\frac{\partial u}{\partial y} + \frac{\partial v}{\partial x}\right). \tag{3}$$

The strain values determined in step 710 can be represented as components of an infinitesimal engineering strain ($E_{ij}$) at each location or point (x, y, z), which can be represented as a tensor of displacement gradients at each corresponding location, as shown in Equation (4):

$$(E_{ij}) = \begin{pmatrix} \frac{\partial u}{\partial x} & \frac{\partial u}{\partial y}+\frac{\partial v}{\partial x} & \frac{\partial u}{\partial z}+\frac{\partial w}{\partial x} \\ \frac{\partial v}{\partial x}+\frac{\partial u}{\partial y} & \frac{\partial v}{\partial y} & \frac{\partial v}{\partial z}+\frac{\partial w}{\partial y} \\ \frac{\partial w}{\partial x}+\frac{\partial u}{\partial z} & \frac{\partial w}{\partial y}+\frac{\partial v}{\partial z} & \frac{\partial w}{\partial z} \end{pmatrix} \tag{4}$$

where the differential terms are the displacement gradients, and u, v, and w are the tri-axial displacement components, in mutually orthogonal directions corresponding to the x, y and z axes, at the monitoring point (x, y, z). The tri-axial displacement components depend on location and time t, i.e., u=u(x,y,z,t), v=v (x,y,z,t), and w=w(x, y, z, t). The strain tensor $E_{ij}$ thus depends on x, y, z, and t.

The displacement gradients depend on the rate of change of the displacement vectors in the respective orthogonal direction, e.g., as shown in Equation (5):

$$\frac{\partial u}{\partial x} = \lim_{\Delta x \to 0}\left(\frac{u(x+\Delta x, t) - (x, t)}{\Delta x}\right) \tag{5}$$

In the analysis process 700, the strains in the strain tensor $E_{ij}$ are determined by determining the various displacement gradients in Equation (4). More than three independent measurements of displacement are used to determine the six displacement gradients in 3D. More than two independent measurements are used in 2D.

The various analysis processes mentioned in step 702 are described hereinafter with reference to FIG. 4, which shows three measurement locations, P, Q and R arranged for making 2D measurements. The explanation below refers primarily to the 2D measurements for simplicity. For 3D measurements, a fourth location is required; however, equivalent processes are used. After an event, the measurement locations P, Q and R move to new locations P', Q' and R' due to the infinitesimal particle motions. Before the motion occurs, locations P and Q are spaced apart by a distance dx along the x axis, and by a distance dy along the orthogonal y axis. The points P and Q have a straight line PQ between them. After a brief motion (also referred to as an infinitesimal motion or movement, i.e., a movement by a distance substantially less than to cause rigid body deformation yet retain continuity of adjacent particles, and thus within the limitations of the infinitesimal approximation), the respective new locations P' and Q' have a new straight line P'Q' between them. The infinitesimal motion thus causes a deformation of the medium surrounding the particles, which causes translation, stretching, contraction and/or rotation of the line PQ into the line P'Q'. The vectorial displacement components of particle P due to the brief motion are represented by $u_1$ and $v_1$ in the orthogonal x and y directions, respectively. Similarly, the infinitesimal displacement components of particle Q are represented by $u_2$ and $v_2$ in the orthogonal x and y directions, respectively. The Q displacement components are related to the P displacement components by addition of the partial derivations of the displacements multiplied by the respective distance components along the orthogonal axes, as shown in Equations (6) and (7):

$$u_2 = u_1 + \frac{\partial u}{\partial x}dx + \frac{\partial u}{\partial y}dy, \tag{6}$$

$$v_2 = v_1 + \frac{\partial v}{\partial x}dx + \frac{\partial v}{\partial y}dy. \tag{7}$$

The relationships in Equations (6) and (7) are relationships between: (i) the strains in a region associated with the displacement gradients; (ii) relative locations of the particles in the group spanned by that region; and (iii) respective infinitesimal displacements of these particles. For example, ∂u/∂x and ∂u/∂y are partial derivatives representing gradients related to strain components in the 2D region spanning points P, Q and R (based on relationships in Equations (1), (2) and (3) above), dx and dy represent relative locations of the points P and Q in 2D, and $u_1$ and $u_2$ represent components of the infinitesimal displacement of the points P and Q in 2D.

In step 710, the processing module 112 uses relationships generally equivalent to those in Equations (6) and (7) for all of the measurement locations that have been selected to define each region. Different equations may be used in different situations for equivalent effects. For example, some generally equivalent relationships may use higher-order terms for the displacement gradients and hence involve more than the minimum number of measurement locations required, e.g., as shown in Equation (7A); this approach can provide an improved estimate of the displacement gradients in some circumstances at the expense of having more measurement locations:

$$-u(x_2, y_0) + 8u(x_1, y_0) - 8u(x_{-1}, y_0) + u(x_{-2}, y_0) = 12h\frac{\partial u(x_0, y_0)}{\partial x} \quad (7A)$$

where the subscripts (−2, −1, 0, 1, 2) refer to sequential measurement locations along a line.

Pure Displacements Analysis Process

In 2D, using the pure displacements analysis process in step 710, the processing module 112 receives the displacement waveforms and positions of the monitors, and determines the four required displacement gradients using the relationships shown in Equations (8)-(11):

$$u_2 - u_1 = \frac{\partial u}{\partial x}(x_2 - x_1) + \frac{\partial u}{\partial y}(y_2 - y_1), \quad (8)$$

$$v_2 - v_1 = \frac{\partial v}{\partial x}(x_2 - x_1) + \frac{\partial v}{\partial y}(y_2 - y_1), \quad (9)$$

$$u_3 - u_1 = \frac{\partial u}{\partial x}(x_3 - x_1) + \frac{\partial u}{\partial y}(y_3 - y_1), \quad (10)$$

$$v_3 - v_1 = \frac{\partial v}{\partial x}(x_3 - x_1) + \frac{\partial v}{\partial y}(y_3 - y_1). \quad (11)$$

Equations (8)-(11) are based on substitution and rearrangement of Equations (6) and (7) for the lines between P and Q, and P and R, and their deformations caused by the particle waves.

The coordinate values of the measurement locations (referred to as the locations of the particles), along the x and y axes, are $x_1$ and $y_1$ for P, $x_2$ and $y_2$ for Q, $x_3$ and $y_3$ for R. These positions are typically measured as the pre-movement positions, but can also be the post-movement positions as the analysis uses an infinitesimal strain approximation.

The outputted displacement gradients represent displacement gradients averaged between the selected measurement locations. Generally, adjacent monitor locations are used to create a dense map of strains if there are many monitors. A coarser analysis is hence possible if desired by using clusters of monitors further apart for the region in which the strain is calculated.

The above equations can be solved using software modules in the analysis machine 130 implementing, for example, a standard singular value decomposition (SVD) method or process. The SVD process solves the system of equations with more equations than unknowns to obtain a solution with a least squares optimization.

An equivalent set of nine linear equations representing lines between the location P and three non-collinear locations Q, R and S are required for determining the strain components in the region spanning the points P, Q, R and S in three dimensions.

Displacements And Rotations Analysis Process

In 2D, using the displacements analysis process in step 710, the processing module 112 solves four simultaneous linear equations that relate the displacements u, v, etc., and the strains ∈ plus a rotation of the particle at each location, as shown in Equations (12)-(15) for the points P, Q and R in the x-y plane:

$$u_2 - u_1 = \in_x (x_2 - x_1) + \in_{xy}(y_2 - y_1) - \omega_z(y_2 - y_1) \quad (12)$$

$$v_2 - v_1 = \in_{xy}(x_2 - x_1) + \in_y(y_2 - y_1) - \omega_z(x_2 - x_1) \quad (13)$$

$$u_3 - u_1 = \in_x(x_3 - x_1) + \in_{xy}(y_3 - y_1) - \omega_z(y_3 - y_1) \quad (14)$$

$$v_3 - v_1 = \in_{xy}(x_3 - x_1) + \in_x(y_3 - y_1) - \omega_z(x_3 - y), \quad (15),$$

where $\omega_z$ is rotation about the z axis in the region spanned by the three points and is related to the sum of the displacement gradients as shown in Equation (16):

$$\omega_z = \frac{1}{2}\left(\frac{\partial v}{\partial x} - \frac{\partial u}{\partial y}\right) \quad (16)$$

The calculation of the desired strains and rotations can be obtained using an SVD method corresponding to that described above.

In 3D, the processing module 112 determines the six unknown strain components from nine independent equations that are equivalent to Equations (12) to (15).

Elongation Analysis Process

Using the elongation analysis process in step 710, the processing module 112 uses relationships based on elongation of lines connecting the locations to determine the strains.

A 2D elongation, e, is the change in length over the original length of the distance between the two points. The elongation measured in the direction of the line joining two points is related to the angle θ of the line measured from the x-axis and to the direction cosines 1 and m according to the relationships in Equations (17) and (18), which apply under conditions of infinitesimal strain.

$$e = \in_x \cos^2 \theta + \in_y \sin^2 \theta + \in_{xy} \sin 2\theta \quad (17)$$

$$e = \in_x l^2 + \in_y m^2 + 2lm \in_{xy} \quad (18)$$

The direction cosines of a vector between the two points are the cosines of the angles between the vector and the three coordinate axes (e.g., the x, y and z axes).

In the elongation analysis process, the processing module 112 solves three equations (i.e., one equation, based on Equation (17) or Equation (18), for each line from the location to the other two locations, e.g., PQ, PR, and QR for the three unknown strain components in Equation (17) or (18).

The elongations and strains can be calculated using an SVD method equivalent to that described above.

In 3D, the expression for the elongation of one line, i.e., equivalent to Equation (18), is as shown in Equation (19):

$$e = \in_x l^2 + \in_y m^2 + \in_z n^2 + 2mn \in_{yz} + 2nl \in_{zx} + 2lm \in_{xy} \quad (19)$$

where l, m, n are the direction cosines. In an analogous way to the 2D case, the six independent elongation estimates determined from the displacement measurements in 3D can be used to solve for the six unknown strain components. Six independent elongation measurements require a minimum of four non-coplanar points in 3D.

Angles Analysis Process

Using the angles analysis process in step 710, the processing module 112 uses relationships between changes in the angles of lines joining pairs of measurement points to determine the strains.

The change in the angle (i.e., the angular change) of the line (or vector) joining two points in 2D that results from infinitesimal strain is related to the displacement gradients in a relationship shown in Equations (20) and (21):

$$\Delta\theta = \frac{\partial v}{\partial x}\cos^2\theta + \frac{1}{2}\left(\frac{\partial v}{\partial y} - \frac{\partial u}{\partial x}\right)\sin 2\theta - \frac{\partial u}{\partial y}\sin 2\theta \quad (20)$$

$$\Delta\theta = l^2\frac{\partial v}{\partial x} + lm\left(\frac{\partial v}{\partial y} - \frac{\partial u}{\partial x}\right) - m^2\frac{\partial u}{\partial y}. \quad (21)$$

where $\theta$ is the angle of the line measured from the x-axis, e.g., as shown for PQ in FIG. 4, and l and m are the direction cosines. The change in angle, $\Delta\theta$, is the change in angle from the original direction of the line to the current direction of the deformed line.

Estimating the 2D strains requires four changes in angle. Thus a minimum of four measurement points is required.

The processing module 112 determines the four unknown partial derivatives (displacement gradients) using the relationships in Equations (20) and (21).

For 3D, the processing module 112 determines angular change $\Delta\theta$ between the lines PQ and P'Q', as shown in FIG. 4, which may be generalised using the relationship shown in Equation (22):

$$\tan\Delta\theta = \left|\frac{\overrightarrow{PQ} \times \overrightarrow{\Delta u}}{\overrightarrow{PQ}\cdot\overrightarrow{PQ} + \overrightarrow{\Delta u}\cdot\overrightarrow{PQ}}\right| \quad (22)$$

where the numerator is the vector cross product of the original vector and the incremental change vector given by the terms involving the displacement gradients in equations of the form of Equation (8) (i.e., $\Delta u = u_2 - u_1$). The denominator involves two vector dot products.

The changes in angles and the strains can be calculated using a method combining SVD and direct calculations.

In 3D, the Equations (20) and (21) are generalised to the 3D case, thus involving the nine displacement gradients, and requiring a minimum of five measurement points to determine the required nine angular changes.

The minimum number of measurement points using the change in angle, to estimate the unknowns is redundant: four points in 2D enable six independent measurements of angle change and five points in 3D enable ten independent measurements—only four and nine measurements, respectively, are actually required.

Mixed Data Analysis Process

Using the mixed data analysis process in step 710, the processing module 112 uses a mixed set of measurements of changes in displacement, elongation or angle change. For example, by using two points in a plane, the processing module can determine:

(i) two equations in the four unknown displacement gradients when changes in displacement of the two points are measured;
(ii) one equation in the three unknown strains which comprise of the four unknown displacement gradients arises when the elongation is measured between the two points; or
(iii) one equation in the three unknown strains which comprise of the four unknown displacement gradients arises when the angular change of the line joining the two points is measured.

At least three non-collinear points are used in 2D and at least four non-coplanar points are used in 3D. The mixed data analysis process can use an SVD, or a similar, processing method, equivalent to that described above.

Example Applications

The analysis process 700 can provide a good approximation to an exact measure of deformation in the medium for certain types of materials, e.g., materials found in mining, exploration, and civil and mechanical engineering such as rock, concrete, steel. For example, for a blast vibration peak particle velocity (PPV) of 5000 mm/s and a ground sonic velocity (c) of 2000 m/s, the deformation gradient may be estimated as about PPV/c=0.0025. In such a case, the second order terms of the deformation gradient (e.g., $$\left(\frac{\partial v}{\partial x}\right)^2 \text{ or } \frac{\partial v}{\partial y}\frac{\partial v}{\partial z}\right)$$

are in the order of $10^{-6}$-$10^{-5}$ which is negligible (<1%) compared to the first order terms of the displacement gradient. Thus the analysis process 700 can be applicable to blast vibration of PPV up to 5000 mm/s for most rock types.

The analysis process 700 can be applied in the far field of a blast where the peak particle velocity is as small as 1 mm/s, as well as to the near field of a blast where the peak particle velocity can be up to 5000 mm/s.

Figure 8:
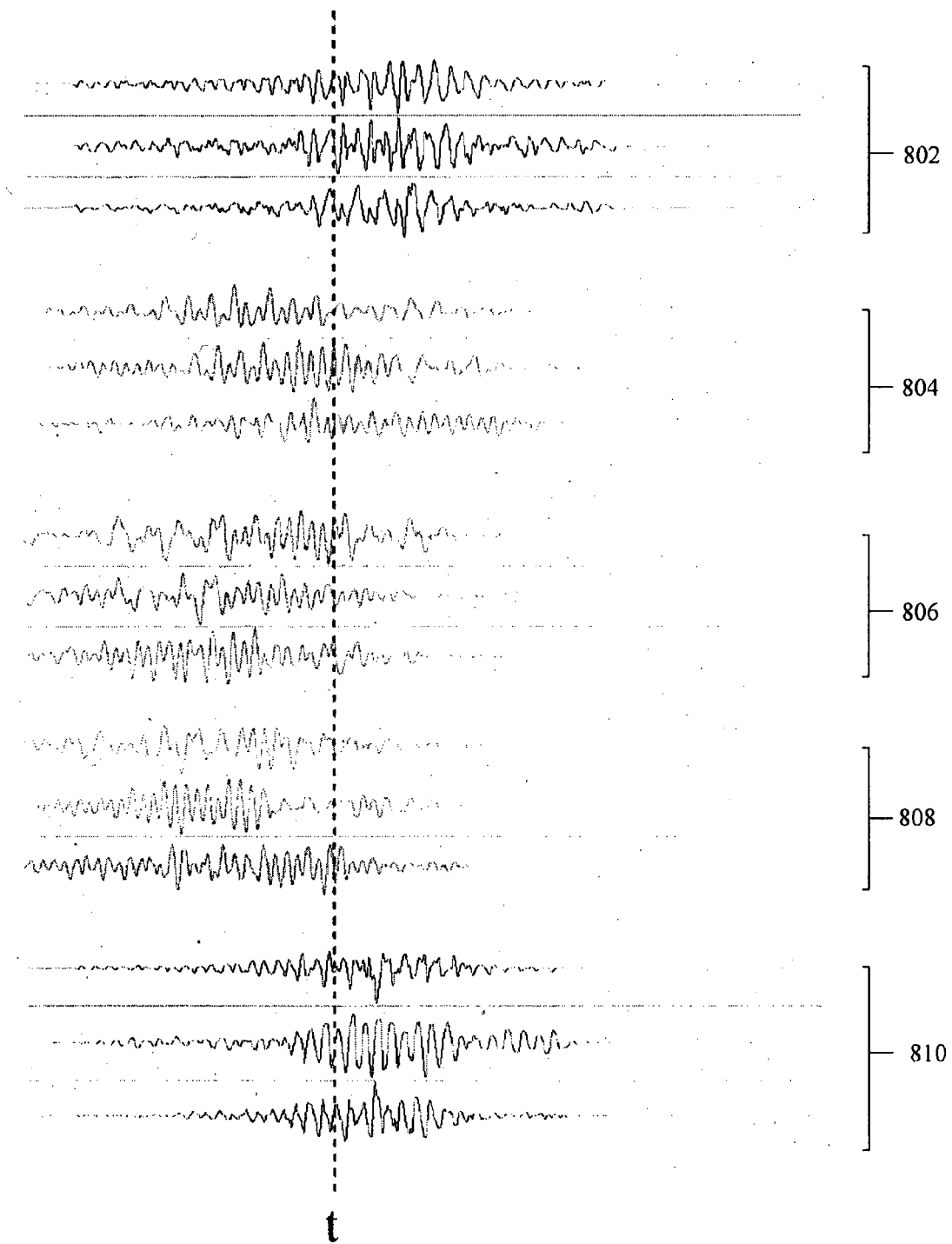
FIG. 8 is a graph of example displacement waveforms generated in the measurement process, shown with displacement on the vertical axis and time on the horizontal axis.
Figure 9:
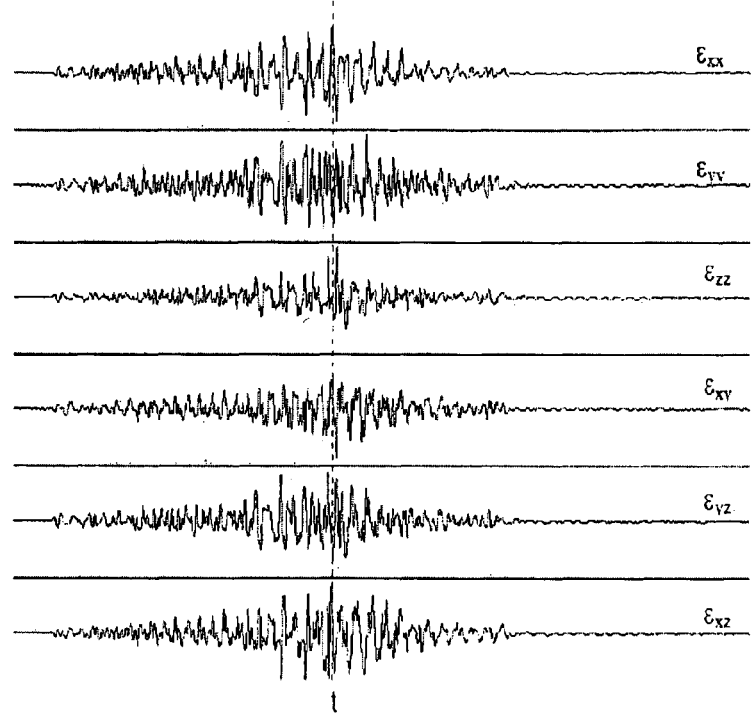
FIG. 9 is a graph of example strain waveforms generated in the analysis process, shown with strain on the vertical axis and time on the horizontal axis.

In an example, five sets 802, 804, 806, 808 and 810 of synchronized tri-axial vibration displacement waveforms, shown in FIG. 8, were measured at five different non-coplanar measurement points. Using the analysis process 700, the normal and shear strain components for the region were determined. At each time instance t, the means of the six components of the second-order strain tensor were generated. There was redundancy in the number of measurement points that was handled automatically by the SVD process.

Experimental Example

In an experimental example, six monitors were placed in soft ground on mounting blocks. The mounting blocks were buried to have a firm coupling to the ground. The six monitors were placed around a test region with a 3-m radius. The monitor locations were selected to ensure no more than three monitors occupied the same geometrical plane (to achieve an accurate solution for the dynamic strain). Each monitor included three orthogonal accelerometers (or one tri-axial accelerometer). Each accelerometer was placed in a horizontal plane confirmed by a bubble level, and the direction of the x-axis of each accelerometer from North was measure for each test. The three-dimensional location of each accelerometer was surveyed with an accurate differential GPS system based on a tripod placed over each monitor.

Figure 10:
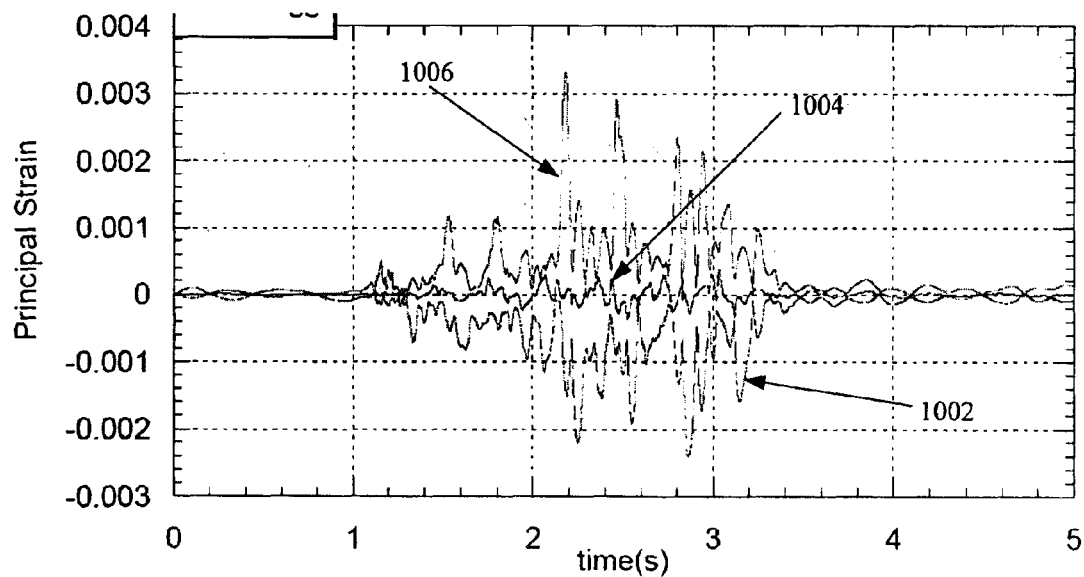
FIG. 10 is a graph of the principal strains generated in an experimental measurement and analysis process, with strain shown on the vertical axis (where tensile strain is shown as positive) and time (in seconds on the horizontal axis)

An example hub including an "eDAQ-lite" (or eDAQ) data collecting unit was used to simultaneous collect up to 20 channels of data with a time synchronization error less than 0.45 µs. The eDAQ unit recorded blast vibration from the six monitors at sampling rates of 2.5 kHz and 5 kHz Blast vibration waveforms were recorded in the eDAQ unit from the accelerometers, and thereafter input to an analysis program, which processed the data and determined the dynamic strains in three dimensions. Each strain component as function of time was determined. The principal strains and their directions were obtained from the program which generated waveforms 1002, 1004, 1006 representing the principal strains S1, S2 and S3 in the test region, as shown in FIG. 10.

Example Computer 500

Figure 5:
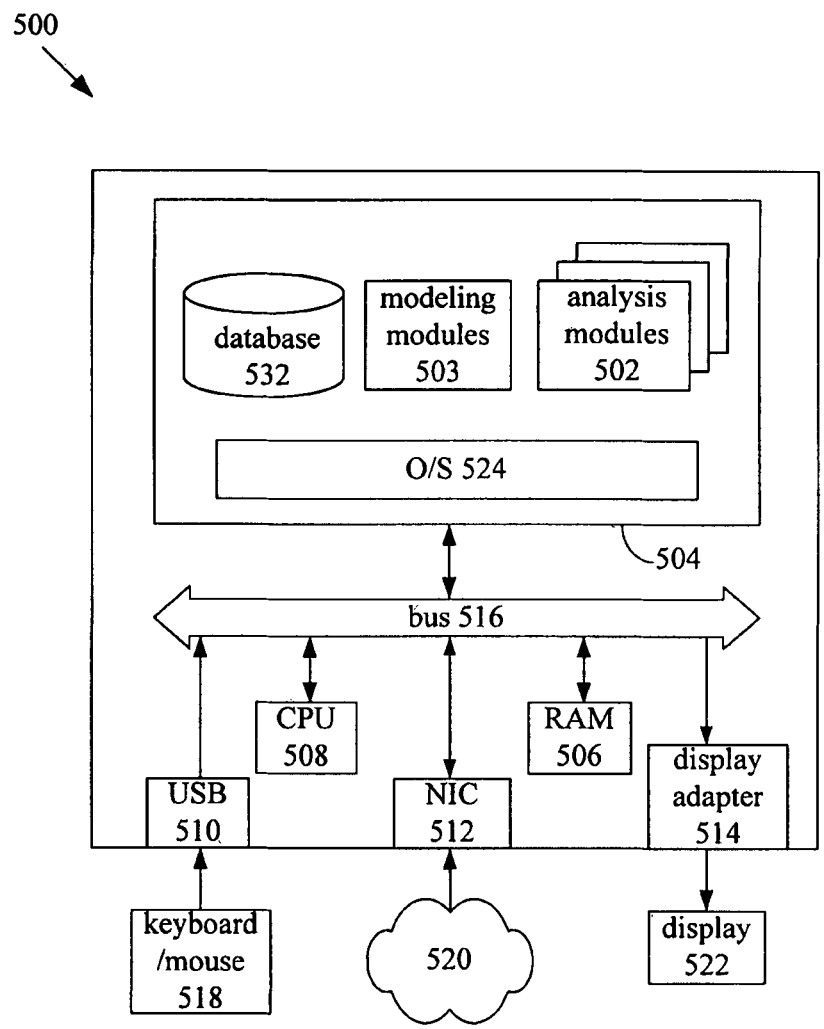
FIG. 5 is a block diagram of a computer of the system.

The analysis machine 130 can be a computer 500, including the modelling modules 503 and a plurality of analysis modules 502, as shown in FIG. 5, which include the modules 110, 112 and 114. The standard computer system 500 can be a commercially available personal computer or server computer system based on a 32-bit or 64-bit Intel architecture or other, and the processes and/or methods executed or performed by the analysis machine 130 are implemented in the form of programming instructions of one or more software components or modules (including the analysis modules 502) stored on non-volatile (e.g., hard disk) computer-readable storage 504 associated with the computer system 500. Alternatively, at least portions of the software modules 502 could be implemented as one or more dedicated hardware components, such as application-specific integrated circuits (ASICs) and/or field programmable gate arrays (FPGAs).

The computer system 500 includes at least one or more of the following standard, commercially available, computer components, all interconnected by a bus 516: random access memory (RAM) 506, at least one computer processor 508, and external computer interfaces. The external computer interfaces include: universal serial bus (USB) interfaces 510 (at least one of which is connected to one or more user-interface devices, such as a keyboard, a pointing device (e.g., a mouse 518 or touchpad), a network interface connector (NIC) 512 which connects the computer system 500 to a data communications network such as the Internet 520, and a display adapter 514, which is connected to a display device 522 such as a liquid-crystal display (LCD) panel device.

The computer system 500 includes a plurality of standard software modules, including: an operating system (OS), e.g., Linux or Microsoft Windows, and structured query language (SQL) modules (e.g., MySQL, available from http://www.mysql.com), which allow data to be stored in and retrieved/accessed from a database 532.

The boundaries between the modules and components in the software modules 502 are exemplary, and alternative embodiments may merge modules or impose an alternative decomposition of functionality of modules. For example, the modules discussed herein may be decomposed into submodules to be executed as multiple computer processes, and, optionally, on multiple computers. Moreover, alternative embodiments may combine multiple instances of a particular module or submodule. Furthermore, the operations may be combined or the functionality of the operations may be distributed in additional operations in accordance with the invention. Alternatively, such actions may be embodied in the structure of circuitry that implements such functionality, such as the micro-code of a complex instruction set computer (CISC), firmware programmed into programmable or erasable/programmable devices, the configuration of a field-programmable gate array (FPGA), the design of a gate array or full-custom application-specific integrated circuit (ASIC), or the like.

Each of the blocks of the flow diagrams of the processes of the computer system 500 may be executed by a module (of software modules 502) or a portion of a module. The processes may be embodied in a machine-readable and/or computer-readable medium for configuring a computer system to execute the process. The software modules may be stored within and/or transmitted to a computer system memory to configure the computer system to perform the functions of the module.

Alternatives

The primary measurements of particle displacement, velocity or acceleration may be provided by transducers other than the traditional vibration measurement sensors such as geophones and accelerometers. For example, dynamic digital photogrammetry, and Doppler interferometry using light or radio waves can measure the desired dynamic kinematic quantities from which elongations and rotations also may be determined.

The analysis system 104 can be integrated with the measurement system 102 (e.g., integrated with the hub 126) to provide a miniaturised (and possibly portable) vibration measurement and analysis system, e.g., for field use.

Example Implementation

An example implementation of the vibration analysis system—with an example processing module written in C++, C# and/or Matlab, and executed on a standard computer processor—generates the dynamic strain tensor from particle displacement measurements based on relationships for an elastic solid in 2D and 3D. The determined strain is assumed to be uniform in the region spanning by the measurement locations. Alternatively, a non-uniform variation of the strain within each region is assumed, and the values in the region are interpolated from the measured displacements using standard methods from finite element analysis of structures. The 2D and 3D solutions for the displacement gradients, and the calculation of derived quantities such as principal strains and rotations, are provided by computer-readable code executed by one or more computer processors.

In the general 3D case a minimum of four non-coplanar measurement locations provide sufficient data to solve for the nine displacement gradients from which the dynamic strain tensor may be determined. In the 2D case a minimum of three non-collinear measurement locations are required to solve for the four displacement gradients under plane strain conditions and the same four displacement gradients plus the Poisson's ratio under plane stress conditions or at a free surface. The strain tensor is generated from the displacement gradients. The determined displacement gradients may be used to calculate the rotations about the standard axes and these may be interpreted as a torsion about the normal to the free surface and also a tilt derived from the other two rotations.

An example arrangement of the motion sensors can be on a free surface of an elastic solid, e.g., on the ground of a mining site. For this arrangement, which can be considered to be a plane stress situation, the system uses a 6 displacement gradients or equivalently 4 in-plane displacement gradients and the medium's Poisson ratio, and uses these to calculate the three surface strains, and the out-of-plane normal strain, based on Poisson's ratio of the medium. In this case, the processing module can determine that the measurement locations are coplanar (within a tolerance), and proceed with 2D processing, as described below.

In the example implementation, ground vibration data (captured via geophones or accelerometers by any of a wide range of monitor types) is converted into displacement waveforms suitable for providing the raw input data needed by the strain calculation algorithm. The input data includes:

(1) coordinates of the measurement locations in a 'global' coordinate system, i.e., one that covers the entire region of interest, such as the site coordinate system in use where the ground vibration data was captured, usually consisting of easting, northing and Reduced Level or RL (for a 2D strain calculation, the x, y and z coordinates of the measurement locations are transformed by the example processing module into a 2D Cartesian system defined in the plane of the measurement points, as described hereinafter); and (2) time-dependent particle displacements at the measurement locations at the same times.

The input files contain vibration data that have been captured at the same time at different measurement locations. The example system determines whether the data are simultaneous, e.g., based on timestamps in the data, and only proceeds if the time instants for the samples match. The vibration data may be time-synchronised using a connected digital acquisition system ("DAQ"), or timing information from each monitor, e.g., using GPS. The vibration data are also sampled at the same sampling rate. The orientations of the 2D or 3D orthogonal measurement axes of each vibration measurement are corrected if necessary so that the axes aligned with the selected global coordinate system. A geometric transformation can be used to transform vibration measurements with different measurement coordinate systems to the global coordinate system. For example, if a sensor is not correctly aligned when the data was captured, then a rotation of the horizontal components of the data about the sensor's vertical axis can be made to bring the data into correct orientation. The example processing module uses at least three input files for a 2D calculation to be possible and at least four files for a 3D calculation to be possible. The user may select whether to use all available locations, or only a subset of them. If a coplanar group (or set) of measurement locations is selected, the system can perform a 2D analysis. If a non-coplanar group (or set) of locations is selected, the system can perform a 3D analysis.

Any measured velocity or acceleration measurements (i.e., waveforms) in the input data are converted to displacement measurements using standard numerical integration tools.

The example processing module is configured to import blast design data from an existing blast design package, e.g., SHOTPlus-i Pro or SHOTPlus 5 Pro used by Orica Mining Services. The blast design software can be used to generate a blast design populated with vibration monitor points corresponding to the measurement locations used in the field. The blast design data can then be imported into the example processing module to obtain 3D coordinates and identifying labels of the measurement locations.

Once the measurement locations data are imported into the example processing module, the synchronized motion measurements are matched to each measurement location, e.g., based on user selections of the motion data files and respective locations.

The example processing module can receive a user selection of which locations of the imported locations to use in generating the output strain data. The example processing module then determines whether the selected measurement locations are collinear or coplanar, e.g., using orthogonal regression to determine the plane of best fit through the measurement points. If selected points are within a small perpendicular distance, the processing module treats these points as being collinear/coplanar. This perpendicular distance, which can be referred to as a "proximity tolerance", can be set by the user to any value, e.g., between 1 mm and 1 m, with a system default of 2 cm. Increasing the proximity tolerance makes it more likely that the processing module will regard all the measurement locations as being collinear/coplanar. If the points are regarded by the example processing module as collinear, the processing halts, and if they are regarded as coplanar, the example processing module proceeds using 2D processing. For 2D processing, the example processing module transforms the 3D locations into a 2D coordinate system in the best-fit plane of the points. The 3D-to-2D transformation is performed using a construction of two orthonormal axes in the plane using a standard algorithm, and then determines the 3D rotation matrix which will transform points from the global coordinate system into the planar system.

The example processing module selects one of the measurement locations to use as the reference location for the strain determination, e.g., based on a user selection, or based on generating a least-squares solution using each monitor point in turn as the reference location and then picking the solution with the smallest sum of squared residuals (SSR).

The example processing module selects a matrix of linear equations representing predetermined relationships between strain in each region, relative locations of ones of the particles surrounding each region, and infinitesimal movements of the ones of the particles.

For 2D processing, the example processing module selects a matrix relationship with the form of Equation (23):

$$\begin{bmatrix} \delta u_1 \\ \delta v_1 \\ \delta w_1 \\ \delta u_2 \\ \delta v_2 \\ \delta w_2 \\ \vdots \\ \delta u_n \\ \delta v_n \\ \delta w_n \end{bmatrix} = \begin{bmatrix} \delta x_1 & \delta y_1 & 0 & 0 & 0 & 0 \\ 0 & 0 & 0 & \delta x_1 & \delta y_1 & 0 \\ 0 & 0 & -\delta x_1 & 0 & 0 & -\delta y_1 \\ \delta x_2 & \delta y_2 & 0 & 0 & 0 & 0 \\ 0 & 0 & 0 & \delta x_2 & \delta y_2 & 0 \\ 0 & 0 & -\delta x_2 & 0 & 0 & -\delta y_2 \\ \vdots & \vdots & \vdots & \vdots & \vdots & \vdots \\ \delta x_n & \delta y_n & 0 & 0 & 0 & 0 \\ 0 & 0 & 0 & \delta x_n & \delta y_n & 0 \\ 0 & 0 & -\delta x_n & 0 & 0 & -\delta y_n \end{bmatrix} \begin{bmatrix} u_{,x} \\ u_{,y} \\ u_{,z} \\ v_{,x} \\ v_{,y} \\ v_{,z} \end{bmatrix} \quad (23)$$

and for 3D processing, the example processing module selects a matrix relationship with the form of Equation (24):

$$\begin{bmatrix} \delta u_1 \\ \delta v_1 \\ \delta w_1 \\ \delta u_2 \\ \delta v_2 \\ \delta w_2 \\ \vdots \\ \delta u_n \\ \delta v_n \\ \delta w_n \end{bmatrix} = \begin{bmatrix} \delta x_1 & \delta y_1 & \delta z_1 & 0 & 0 & 0 & 0 & 0 & 0 \\ 0 & 0 & 0 & \delta x_1 & \delta y_1 & \delta z_1 & 0 & 0 & 0 \\ 0 & 0 & 0 & 0 & 0 & 0 & \delta x_1 & \delta y_1 & \delta z_1 \\ \delta x_2 & \delta y_2 & \delta z_2 & 0 & 0 & 0 & 0 & 0 & 0 \\ 0 & 0 & 0 & \delta x_2 & \delta y_2 & \delta z_2 & 0 & 0 & 0 \\ 0 & 0 & 0 & 0 & 0 & 0 & \delta x_2 & \delta y_2 & \delta z_2 \\ \vdots & \vdots & \vdots & \vdots & \vdots & \vdots & \vdots & \vdots & \vdots \\ \delta x_n & \delta y_n & \delta z_n & 0 & 0 & 0 & 0 & 0 & 0 \\ 0 & 0 & 0 & \delta x_n & \delta y_n & \delta z_n & 0 & 0 & 0 \\ 0 & 0 & 0 & 0 & 0 & 0 & \delta x_n & \delta y_n & \delta z_n \end{bmatrix} \begin{bmatrix} u_{,x} \\ u_{,y} \\ u_{,z} \\ v_{,x} \\ v_{,y} \\ v_{,z} \\ w_{,x} \\ w_{,y} \\ w_{,z} \end{bmatrix} \quad (24)$$

where n is the number of measurement locations, $\delta u_i \equiv u_i - u_k$ are the displacement differences, $\delta x_i \equiv x_i - x_k$, etc. are the coordinate differences of the locations, and $u_{,x} \equiv \partial u/\partial x$ etc. are the displacement gradients.

Equations (23) and (24) are of the form Y=A X. The example processing module populates the matrix A using the measurement locations. Then, for each time step, the example processing module executes the following processing steps:

1. populate the matrix Y with the measured displacements relative to the reference point;
2. solve for X using a standard least-squares solver;
3. determine an estimated standard error in the displacement gradients (i.e., the components of X) using a standard module (e.g., Matlab's "Iscov" module) that computes ordinary least-squares solutions (optionally in the presence of known covariance);
4. determine estimated standard errors in the strain components $\in_{i,j}$ using the standard errors in the displacement gradients in X;
5. determine an SSR and Q-factor using standard relationships (these quantities can be used in iterative implementations of these processing steps to compare and select preferred initial conditions, e.g., different starting reference points, or different best-fit planes for the 2D processing);
6. determine rotation and tilt angles using standard relationships;
7. determine the normal and shear strains $\in_{ij}$ in 3D using a relationship with the form of Equation (25):

$$\varepsilon = \begin{bmatrix} \varepsilon_x & \varepsilon_{xy} & \varepsilon_{xz} \\ \varepsilon_{xy} & \varepsilon_y & \varepsilon_{yz} \\ \varepsilon_{xz} & \varepsilon_{yz} & \varepsilon_z \end{bmatrix} \equiv \begin{bmatrix} u_{,x} & \frac{1}{2}(u_{,y}+v_{,x}) & \frac{1}{2}(u_{,z}+w_{,x}) \\ \frac{1}{2}(u_{,y}+v_{,x}) & v_{,y} & \frac{1}{2}(v_{,z}+w_{,y}) \\ \frac{1}{2}(u_{,z}+w_{,x}) & \frac{1}{2}(v_{,z}+w_{,y}) & w_{,z} \end{bmatrix} \quad (25)$$

or determine the normal and shear strains in 2D using the upper left-hand 2×2 submatrix in Equation (26):

$$\varepsilon = \begin{bmatrix} u_{,x} & \frac{1}{2}(u_{,y}+v_{,x}) & 0 \\ \frac{1}{2}(u_{,y}+v_{,x}) & v_{,y} & 0 \\ 0 & 0 & \alpha(u_{,x}+v_{,y}) \end{bmatrix} \quad (26)$$

which assumes that the out-of-plane stresses are zero;
8. determine the principal strains by calculating the eigenvalues of the strain matrix E determined above;
9. store the determined data; and
10. determine the following quantities "on the fly" from the stored data using standard relationships: strain dilatation, maximum shear strain, octahedral shear strain, and tilt.

Figure 11:
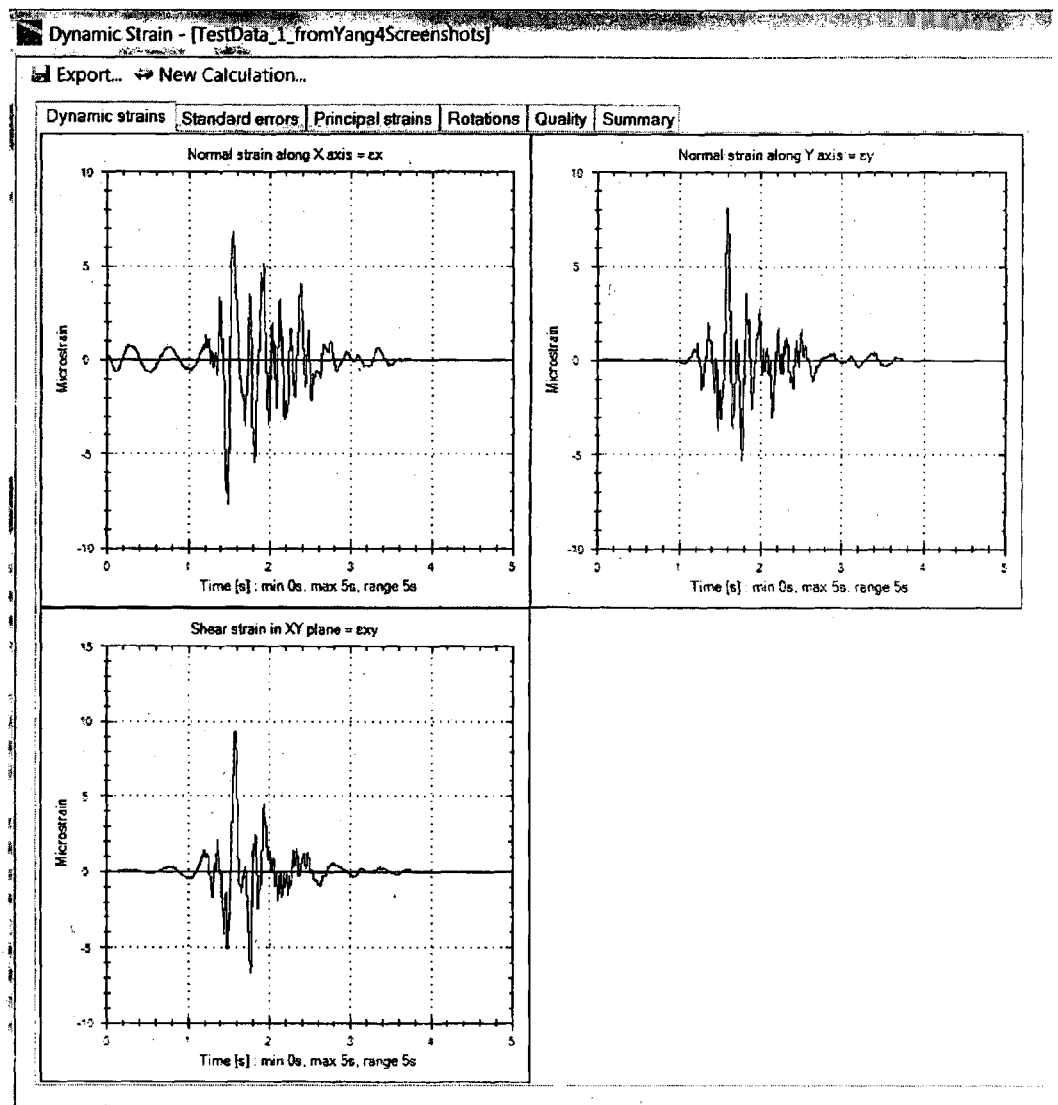
FIG. 11 is a screenshot of a user interface of an example processing module of the system.

The strain matrix results are stored in the example storage, displayed to the user on the example display in graphical form, e.g., the various determined quantities can be plotted as a function of time on separate graphs, as shown in FIG. 11.

Interpretation

Many modifications will be apparent to those skilled in the art without departing from the scope of the present invention.

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

Related Application

The originally filed specification of the following related application is incorporated by reference herein in its entirety: U.S. Provisional Application No. 61/558,978, filed 11 Nov. 2011, entitled "Vibration Analysis".

The invention claimed is:

1. A process for vibration analysis of a man-made event in a medium, including the steps of:
   receiving, by an analysis machine, motion data representing synchronized motion measurements of particle motion due to the man-made event in two or three orthogonal dimensions over a selected period of time at a plurality of different measurement locations, wherein the synchronized motion measurements are detected and measured by motion sensors in the medium in response to the man-made event and transmitted as data over a communications connection, wherein the synchronized motion measurements are synchronized in time;
   determining, by the analysis machine, one or more strain waveforms in two or three orthogonal dimensions respectively in a plurality of regions spanning the plurality of measurement locations by processing the motion measurements, based on relationships between:
   displacement differences, elongations, and/or angular changes between the selected measurement locations for each regional;
   at least one displacement gradient, strain component or rotation in each of the regions; and
   generating, by the analysis machine, strain data representing the strain waveforms.

2. The process of claim 1, including any one or more of:
   determining, by the analysis machine, stress waveforms in the regions spanning the measurement locations, based on the strain waveforms;
   removing, by the analysis machine, low-frequency artefacts from motion waveforms based on the motion measurements; and
   selecting parameters for making the motion measurements, including any one or more of the following steps:
   selecting a spacing of the measurement locations;
   selecting a sampling rate for the motion measurements; and
   selecting a sampling duration based on the selected period of time.

3. The process of claim 1, wherein:
   the motion measurements are synchronized using timing signals from a single source; or
   the measurement locations include locations in the near field of mechanical waves associated with the particle motion; or
   the motion measurements include displacement measurements, velocity measurements and/or acceleration measurements made by motion sensors at the measurement locations, measured in the orthogonal dimensions.

4. The process of claim 1, including generating, by the analysis machine, a two-dimensional (2D) or three-dimensional (3D) image of strain in the regions.

5. The process of claim 1, including determining, by the analysis machine, displacement values at the measurement locations using the motion measurements.

6. The process of claim 5, including determining, by the analysis machine, strain values in the strain waveforms using the displacement gradients or the strain components between the measurement locations based on the respective displacement values.

7. The process of claim 6, including solving, by the analysis machine, relationships between:
   the displacement gradients or the strain components; and
   at least three non-collinear ones of the measurement locations for 2D regions, or at least four non-coplanar ones of the measurement locations for 3D regions.

8. The process of claim 7, including:
   simultaneously solving, by the analysis machine, more than three independent equations for 2D regions; or
   simultaneously solving, by the analysis machine, more than six independent equations for 3D regions, to determine the strain values,
   including optionally solving the equations using a matrix solution method, optionally including a singular value decomposition process.

9. The process of claim 7,
   wherein the relationships include linear relationships between:
   (i) coordinate values of selected ones of the measurement locations;
   (ii) the displacement values of the selected measurement locations; and
   (iii) the displacement gradients in the regions spanning the selected measurement locations, or
   wherein the relationships include linear relationships between:
   (i) coordinate values of selected ones of the measurement locations;
   (ii) the displacement values of the selected measurement locations;
   (iii) the displacement gradients in the regions spanning the selected measurement locations; and
   (iv) the rotations of the regions spanning the selected measurement locations, or
   wherein the relationships include linear relationships between: (i) the elongations between selected ones of the measurement locations; (ii) the displacement gradients in the regions spanning the selected measurement locations; and (iii) direction cosines of the vectors, or
   wherein the relationships include linear relationships between: (i) the angular changes between selected ones of the measurement locations; (ii) the displacement gradients in the regions spanning the selected measurement locations; and (iii) direction cosines of the vectors.

10. The process of claim 9, wherein the selected ones of the measurement locations are adjacent ones.

11. A process for vibration analysis of a man-made event in a medium, including:
    receiving, by an analysis machine, motion data representing synchronized motion measurements of particle motion due to the man-made event at a plurality of measurement locations, wherein the synchronized motion measurements are from motion sensors in the medium, wherein the synchronized motion measurements are synchronized in time;
    selecting three or more non-collinear ones of the measurement locations for at least one two-dimensional (2D) strain value, or selecting four or more non-coplanar ones of the measurement locations for at least one three-dimensional (3D) strain value; and
    generating, by the analysis machine, strain data representing the 2D or 3D strain value in a region spanning the selected measurement locations, wherein the generating uses the motion measurements and is based on relationships between:
    displacement differences, elongations, and/or angular changes between the selected measurement locations; and
    at least one displacement gradient, strain component or rotation in the region.

12. The process for vibration analysis of claim 11, wherein the step of generating the strain data includes the steps of:
    determining, by the analysis machine, the strain components of the strain value using vector components of the motion measurements;
    determining, by the analysis machine, at least one of the displacement gradients in the region using the motion measurements and spacings between the measurement locations; and
    determining, by the analysis machine, the strain value using the at least one displacement gradient.

13. The process for vibration analysis of claim 11, wherein
    the particle motion is linear motion or angular motion; or
    the selecting of the ones of the measurement locations includes determining whether available measurement locations are coplanar within a selected tolerance level.

14. An analysis system including modules configured to perform the process of claim 1.

15. A computer-readable storage media, including computer-readable instructions configured to control at least one microprocessor to perform the process of claim 1.

16. The process of claim 1:
    wherein the particles are displaced by a blast in two or three orthogonal dimensions, and the receiving is over a selected period of time after the blast, wherein the motion measurements represent relative displacements; and
    wherein the process includes the determining the strain waveforms using:
    data representing the measurement locations, and
    a predetermined relationship between strain in each region, relative locations of ones of the particles surrounding each region, and infinitesimal movements of the ones of the particles.

17. A system for vibration analysis of blasting, including:
    a plurality of sensors configured to generate synchronised motion measurements representing displacements at respective measurement locations in a medium due to vibration waves caused by at least one blasting event;
    a measurement hub configured to receive signals representing the motion measurements from the sensors over a selected period of time after the event; and
    at least one processing module configured to generate, based on the synchronised motion measurements and the measurement locations, strain data representing strain in at least one region spanning the measurement locations,
    wherein:
    the measurement locations are non-collinear, the synchronised motion measurements represent displacements in two orthogonal directions, and the processing module is configured to generate the strain data in two orthogonal directions, or
    the measurement locations are non-coplanar, the synchronised motion measurements represent displacements in three orthogonal directions, and the processing module is configured to generate the strain data in three orthogonal directions.

18. The system of claim 17, wherein the plurality of measurement locations includes a plurality of groups of the measurement locations, and wherein the processing module is configured to generate strain data representing strain in a region spanning each group, and
wherein:
the measurement locations in each group are non-collinear, the synchronised motion measurements represent displacements in two orthogonal directions, and the processing module is configured to generate the strain waveforms in two orthogonal directions; or
the measurement locations in each group are non-coplanar, the synchronised motion measurements represent displacements in three orthogonal directions, and the processing module is configured to generate the strain waveforms in three orthogonal directions.

19. The system of claim 17, wherein:
the plurality of strain waveforms are generated using at least one predetermined relationship between strain in a region spanning the measurement locations, relative locations of the measurement locations, and infinitesimal movement of the particles; or
the medium includes at least one structure and/or geological material.

20. A process for vibration analysis of blasting, including the steps of:
generating synchronised motion measurements representing displacements at respective measurement locations in a medium due to vibration waves caused by at least one blasting event;
receiving signals representing the motion measurements from the sensors over a selected period of time after the event; and
generating, based on the synchronised motion measurements and the measurement locations, strain data representing strain in at least one region spanning the measurement locations
wherein:
the measurement locations are non-collinear, the synchronised motion measurements represent displacements in two orthogonal directions, and the processing module is configured to generate the strain data in two orthogonal directions, or
the measurement locations are non-coplanar, the synchronised motion measurements represent displacements in three orthogonal directions, and the processing module is configured to generate the strain data in three orthogonal directions.

21. A system for vibration analysis of blasting, including:
an analysis machine including programming instructions that cause the analysis machine to:
receive motion data representing synchronised motion measurements from a plurality of sensors over a selected period of time after at least one blasting event, wherein the data representing motion measurements are based on signals received from a plurality of sensors configured to generate the synchronised motion measurements representing displacements at respective measurement locations in a medium due to vibration waves caused by the blasting event; and
generate, based on the synchronised motion measurements and the measurement locations, strain data representing strain in at least one region spanning the measurement locations,
wherein:
the measurement locations are non-collinear, the synchronised motion measurements represent displacements in two orthogonal directions, and the processing module is configured to generate the strain data in two orthogonal directions, or
the measurement locations are non-coplanar, the synchronised motion measurements represent displacements in three orthogonal directions, and the processing module is configured to generate the strain data in three orthogonal directions.

22. A process for vibration analysis of blasting, including:
receiving, by an analysis machine, motion data representing synchronised motion measurements from a plurality of sensors over a selected period of time after at least one blasting event, wherein the motion data representing motion measurements are based on signals received from a plurality of sensors configured to generate the synchronised motion measurements representing displacements at respective measurement locations in a medium due to vibration waves caused by the blasting event; and
generating, by the analysis machine, based on the synchronised motion measurements and the measurement locations, strain data representing strain in at least one region spanning the measurement locations,
wherein:
the measurement locations are non-collinear, the synchronised motion measurements represent displacements in two orthogonal directions, and the processing module is configured to generate the strain data in two orthogonal directions, or
the measurement locations are non-coplanar, the synchronised motion measurements represent displacements in three orthogonal directions, and the processing module is configured to generate the strain data in three orthogonal directions.

23. A system for vibration analysis of blasting, including:
a plurality of sensors configured to generate synchronised motion measurements representing displacements at respective measurement locations in a medium due to vibration waves caused by at least one blasting event;
a measurement hub configured to receive signals representing the motion measurements from the sensors over a selected period of time after the event; and
computer-readable storage and at least one display configured to receive and display strain data representing strain in at least one region spanning the measurement locations,
wherein:
the strain data are generated based on the synchronised motion measurements and the measurement locations;
the measurement locations are non-collinear, the synchronised motion measurements represent displacements in two orthogonal directions, and the processing module is configured to generate the strain data in two orthogonal directions, or
the measurement locations are non-coplanar, the synchronised motion measurements represent displacements in three orthogonal directions, and the processing module is configured to generate the strain data in three orthogonal directions.

24. A process for vibration analysis of blasting, including the steps of:
- generating synchronised motion measurements representing displacements at respective measurement locations in a medium due to vibration waves caused by at least one blasting event;
- receiving signals representing the motion measurements from the sensors over a selected period of time after the event; and
- receiving strain data representing strain in at least one region spanning the measurement locations, wherein:
- the strain data are generated based on the synchronised motion measurements and the measurement locations;
- the measurement locations are non-collinear, the synchronised motion measurements represent displacements in two orthogonal directions, and the processing module is configured to generate the strain data in two orthogonal directions, or
- the measurement locations are non-coplanar, the synchronised motion measurements represent displacements in three orthogonal directions, and the processing module is configured to generate the strain data in three orthogonal directions.

* * * * *